(12) United States Patent
Avdeef et al.

(10) Patent No.: US 8,119,998 B2
(45) Date of Patent: Feb. 21, 2012

(54) METHODS AND SYSTEMS FOR IN SITU PHYSICOCHEMICAL PROPERTY TESTING

(75) Inventors: Alex Avdeef, Cambridge, MA (US); Dmytro Voloboy, Chelmsford, MA (US); Deren J. Dohoda, Stoneham, MA (US); Per E. Nielsen, Westlake, OH (US); Michael J. DeMaria, South Boston, MA (US)

(73) Assignee: Pion, Inc., Billerica, MA (US)

( * ) Notice: Subject to any disclaimer, the term of this patent is extended or adjusted under 35 U.S.C. 154(b) by 0 days.

(21) Appl. No.: 12/811,666

(22) PCT Filed: Dec. 23, 2008

(86) PCT No.: PCT/US2008/088211
§ 371 (c)(1),
(2), (4) Date: Jul. 2, 2010

(87) PCT Pub. No.: WO2009/088781
PCT Pub. Date: Jul. 16, 2009

(65) Prior Publication Data
US 2010/0288944 A1    Nov. 18, 2010

Related U.S. Application Data

(60) Provisional application No. 61/019,146, filed on Jan. 4, 2008.

(51) Int. Cl.
*G01N 21/64*    (2006.01)
(52) U.S. Cl. .................................. 250/461.1
(58) Field of Classification Search ............. 250/461.1, 250/461.2, 458.1, 459.1
See application file for complete search history.

(56) References Cited

U.S. PATENT DOCUMENTS

| | | | |
|---|---|---|---|
| 4,538,460 A | 9/1985 | Schettler, Jr. | |
| 5,344,042 A | 9/1994 | Crosby et al. | |
| 6,176,609 B1 | 1/2001 | Cleveland et al. | |
| 6,437,345 B1 * | 8/2002 | Bruno-Raimondi et al. | 250/458.1 |
| 6,569,686 B2 | 5/2003 | Avdeef et al. | |

(Continued)

OTHER PUBLICATIONS

International Search Report for PCT/2008/088211 dated Feb. 24, 2009.

(Continued)

*Primary Examiner* — Kiho Kim
(74) *Attorney, Agent, or Firm* — Rajesh Vallabh; Foley Hoag LLP

(57) ABSTRACT

An apparatus for evaluating physicochemical properties of sample materials contained in an array of vessels includes: a light detector; a light source for transmitting a light beam through the sample material in a vessel to the light detector; an analyzer for processing data from the light detector to determine concentration-related properties of the sample material as a function of time; and a mixing system. The mixing system includes: a plurality of magnetic stirrer elements, each for being placed in a sample material in a different one of the array of vessels; an array of magnetic drive elements, each associated with a different one of the array of vessels and being magnetically coupled with a magnetic stirrer element in an associated vessel; and a drive mechanism coupled to the array of magnetic drive elements for simultaneously moving each of the magnetic drive elements relative to an associated vessel.

34 Claims, 20 Drawing Sheets

Belt Drive Device for Magnet Plate

U.S. PATENT DOCUMENTS

| | | | |
|---|---|---|---|
| 7,234,365 | B2 | 6/2007 | Carlson et al. |
| 2002/0004244 | A1 | 1/2002 | Avdeef et al. |
| 2002/0132353 | A1 | 9/2002 | Tamura et al. |
| 2004/0265173 | A1* | 12/2004 | Matsumoto et al. ............ 422/64 |
| 2005/0287679 | A1 | 12/2005 | Pawliszyn |
| 2006/0104862 | A1 | 5/2006 | Pages Pinyol |
| 2007/0019502 | A1 | 1/2007 | Foley et al. |
| 2007/0251336 | A1 | 11/2007 | Nielsen et al. |
| 2008/0241914 | A1* | 10/2008 | Roh et al. ................... 435/307.1 |
| 2008/0252886 | A1 | 10/2008 | Bodenstaff et al. |

OTHER PUBLICATIONS

Avdeef et al. "PAMPA—a Drug Absorption in vitro Model. 11. Matching the in vivo Unstirred Water Layer Thickness by Individual-Well Stirring in Microtitre Plates." Eur. J. Pharm. Sci., 2004, 22, 365-374.

Avdeef et al. "Dissolution and solubility." In: Comprehensive Medicinal Chemistry II, vol. 5. Elsevier: Oxford, UK, 2007, pp. 399-423.

Http://en.wikipedia.org/wiki/Stir_bar, Oct. 2, 2008.

* cited by examiner

Belt Drive Device for Magnet Plate

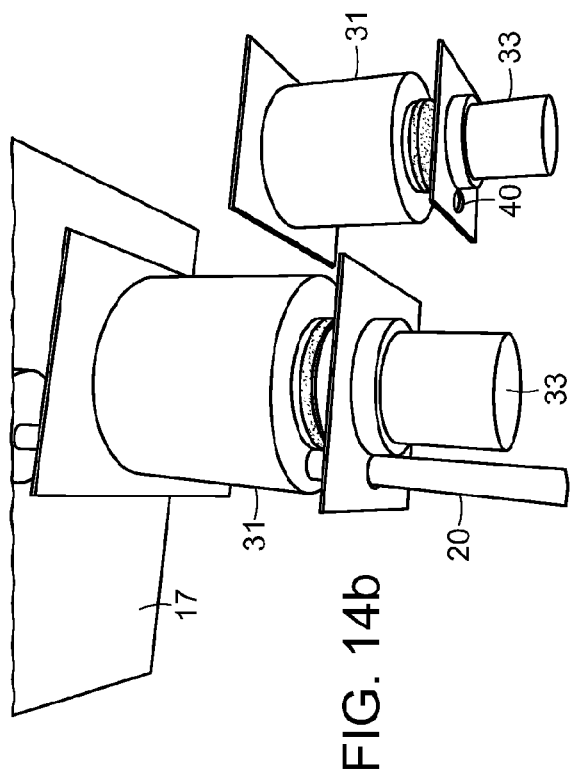
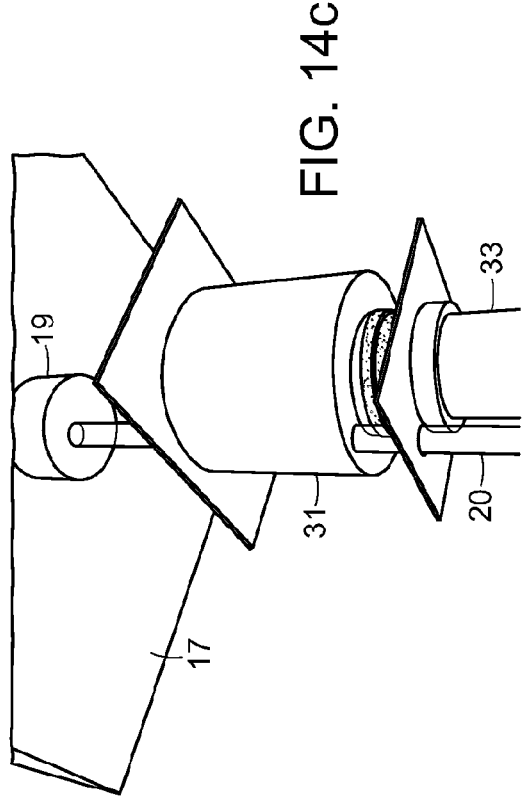
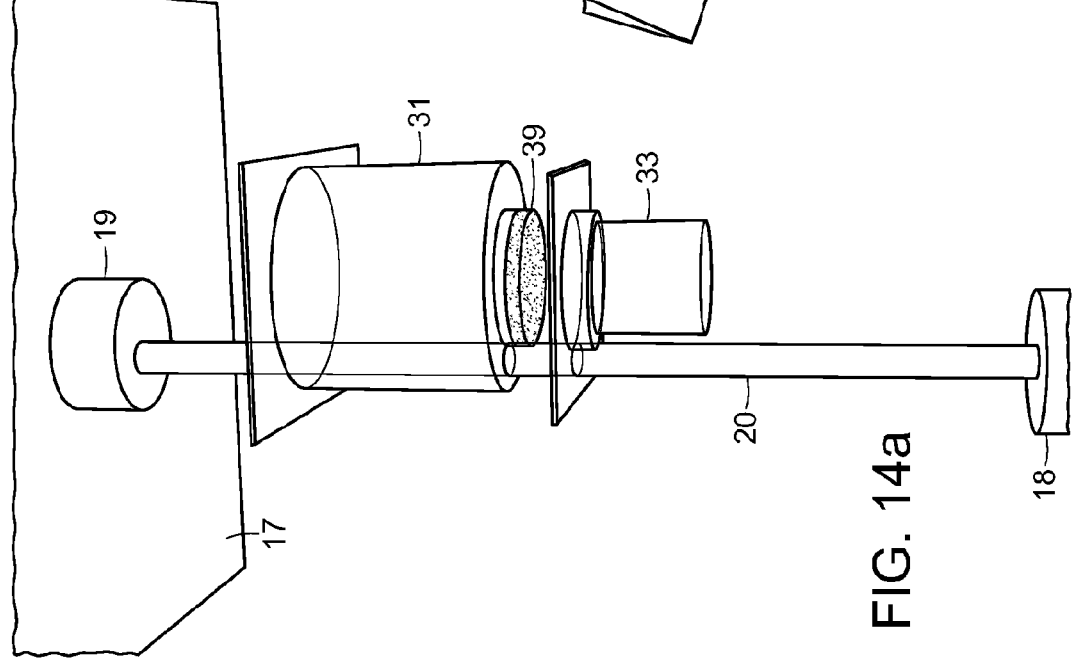
FIG. 14a
FIG. 14b
FIG. 14c

METHODS AND SYSTEMS FOR IN SITU PHYSICOCHEMICAL PROPERTY TESTING

RELATED APPLICATIONS

This application claims priority from PCT/US2008/088211, filed on Dec. 23, 2008, entitled METHODS AND SYSTEMS FOR IN SITU PHYSICOCHEMICAL PROPERTY TESTING, which in turn claims priority to U.S. Provisional Patent Application No. 61/019,146, filed on Jan. 4, 2008, entitled METHODS AND SYSTEMS FOR IN SITU PHYSICOCHEMICAL PROPERTY TESTING, both of which are hereby incorporated by reference.

STATEMENT AS TO FEDERALLY SPONSORED RESEARCH

This invention was made in part with Government support under Grant Number R44 MH75211 from the National Institutes of Health. The Government may have certain rights in the invention.

FIELD OF THE INVENTION

The present application relates to the field of research and development (R&D) of soluble and membrane permeable forms of chemical compounds, such as drug candidates. More particularly, the present application relates to methods and systems for rapid, noninvasive, and in situ evaluation of physicochemical characteristics of compounds (e.g., drug candidates) including: (a) dissolution (i.e., time-dependent solubilization), (b) equilibrium and/or kinetic solubility, (c) precipitation (i.e., time-dependent formation of solid from a solution), and (d) membrane permeability.

BACKGROUND OF THE INVENTION

Human intestinal absorption of chemical compounds can depend simultaneously on several key properties: dissolution, precipitation, solubility, permeability, and, if the compound is ionizable—pKa. This association is exemplified by the compound classification approaches well known to those in pharmaceutical research, e.g., the Absorption Potential, the Biopharmaceutics Classification System, and the Maximum Absorbable Dose classification.

In pharmaceutical research, looking for a new drug typically takes place in three stages: exploration, discovery, and development. In the first stage, the understanding of the disease state is accumulated, a therapeutic target is selected, and a biological screening assay is developed. The discovery stage begins with 'hits' finding, where a company's library of compounds is screened for the IC50 value, the concentration of the compound required to displace 50% of a reference ligand from a target receptor. In the course of a year at a large pharmaceutical company, it is not uncommon to have 100,000 to 1,000,000 library compounds tested against a particular target, which is usually a receptor site on a protein molecule. Of the molecules tested for biological activity, about 3,000 to 10,000 are typically found to be active (hits). The initial part of the discovery step is called 'lead' generation, where the most promising subset of the hits is selected for further testing. Of the 3,000-10,000 potent molecules, about 400 make it to this step. The selection of leads takes into account biopharmaceutic properties of the hits, such as measured aqueous solubility, octanol-water partition coefficients, plasma stability, human serum protein binding, cytochrome P450 inhibition (oxidative metabolism), liver microsome assay (general metabolism), and membrane permeability, using an in vitro cultured-cell model, such as Caco-2. These various tests filter out many molecules with unfavorable biopharmaceutic ADME properties (absorption, distribution, metabolism, and excretion). Most companies perform fast ADME screens in the hits-to-leads transition to aid in "go—no go" decisions. The selected 400 lead compounds are expected to have good in vivo pharmacokinetic (PK) behavior in animal models developed later. But many of the molecules will underperform in laboratory animals, and will be rejected. In lead optimization, the compounds are rigorously tested for in vitro ADME properties, central nervous system (CNS) penetration, selectivity against other similar targets, as well as for cytotoxicity. In the final stages of optimization, where rodent in vivo PK measurements are done, metabolic profiles are developed, and additional animal model toxicity tests are performed, about twelve promising 'candidate' molecules typically survive to enter pre-clinical development, where dosage form design and human PK, safety, and effectiveness testing begin. During the subsequent clinical phases, the number of clinical development molecules dwindles down to about one, a considerable and costly downsizing from the original 400 promising leads.

ADME was the single largest cause of attrition in drug development, accounting for up top 40% of the failures, based on a 1997 study. Since the early 2000s, methods and systems for estimating ADME properties have been introduced, and this has led to significant reductions in the ADME-based attrition rates, benefiting the industry by reducing costs and the consumers by helping to get better drugs to market in less time.

The present application relates particularly to four important physicochemical properties related to ADME: dissolution, precipitation, solubility, and permeability. Collectively, these are properties underlying drug absorption—the 'A' in ADME.

Dissolution (also herein referred to as solubilization), refers to a dynamic process involving the kinetics by which a chemical compound dissolves into a given medium (e.g., solvent). Related to this is solubility, either equilibrium solubility (of the thermodynamically most-stable form of the compound) and/or kinetic solubility (of the active polymorph or salt form of the compound). Also related to this is precipitation, which refers to a dynamic process where a solid in an active polymorphic form first dissolves but then (often, spontaneously) precipitates as a new solid in a more stable polymorphic form. Precipitation is also effected when a supersaturated solution of a compound starts to precipitate a solid form of the compound, usually in a particular polymorphic form. Precipitation may also be triggered following an initial process of dissolution, when a dissolved compound is exposed to a changed solution (e.g., by alteration of pH of the medium, or ionic strength, or buffer constituents, or other additives), such that the compound becomes supersaturated and begins to precipitate as a solid. In this view, precipitation and dissolution are inversely related processes, which can be studied by similar analytical methods and systems. Viewed from the perspective of the resulting solution, dissolution can be characterized by the time-rate-of-change in concentration of the compound in the solution over a dissolution period. In contrast, solubility most often refers to an equilibrium condition (e.g., a time-invariant thermodynamic value) and particularly refers to how much of a sample compound will dissolve into a given medium under conditions in which thermodynamic equilibrium is achieved. Compounds that have a high solubility will generally demonstrate faster dissolution than compounds of lower solubility. However, dissolution characteristics may not directly correlatable to solubility, and valuable information about compounds can be obtained by examining dissolution profiles, in addition to overall solubility data. Dissolution testing of compounds is typically practiced by dissolving at least a portion of a compound in a solvent to form a solution that has a varying concentration of the compound over a dissolution period. The concentrations of the compound dissolved in solution are measured at various times during the dissolution period. This information, taken collectively, represents a time-dependent dissolution profile. If allowed enough compound and enough time to dissolve to reach saturation (i.e., indicated by the presence of excess solid suspended in the solution at equilibrium), one could also measure solubility. In addition, the kinetic solubility of the active polymorph or salt form of the compound may be estimated from the initial dissolution characteristics. However, a dissolution profile can be determined without necessarily determining solubility. Dissolution and precipitation testing is known in many fields, but is of particular significance with respect to drug candidates.

In addition, the present application relates to the measurement of membrane permeability of compounds (also herein referred to as permeability), referring to a dynamic process involving the kinetics by which a compound is transported across a membrane barrier in a permeation cell comprising two solutions in contact with a semi-permeable membrane that lies between and separates the two solutions.

Dissolution testing is required as quality control (QC) for marketed pharmaceutical dosage forms in which gastrointestinal absorption of the drug is necessary for the desired therapeutic effect. The U.S. Pharmacopoeia (USP), through its system of monographs, is one well-known standard source of methods for dissolution and drug release testing. USP dissolution methods employ large volumes of dissolution media (usually 500 or 900 mL), continuously agitated and maintained at 37° C. At fixed time intervals, a small aliquot of sample is taken from each solution vessel, by a multi channeled pumping system, then filtered, and transported to a sample vial for subsequent spectrophotometric or high pressure liquid chromatography (HPLC) analysis. Plotting the percentage of dissolution of a pharmaceutical dosage form as a function of time results in a dissolution profile.

Apart from the above QC applications, dissolution testing is also used during drug formulation development (FD). Precipitation studies often accompany those of dissolution, especially when polymorphic transformations are suspected or are known to occur.

The need for dissolution testing may even be emerging further upstream, in drug discovery (DD). Although high-throughput methods in DD have increased the speed of identification of biologically active compounds, bottlenecks have emerged, impeding timely introduction of new drugs to market. One such bottleneck is the identification of drug candidates that are soluble and/or that have an appropriate rate of solubilization in an aqueous solution such as water or buffered water. Low solubility and/or solubilization of a drug candidate can be problematic because it can make the drug difficult to deliver effectively in a biological system, thus reducing bioavailability. It has been estimated that as many as 12-40% of drug candidates fail in animal toxicology and/or clinical trials because they are poorly soluble and/or have poor solubilization.

Approaches to solve solubility and/or solubilization problems include identification of salt forms or related structures (e.g., polymorphs) of the drug candidate that may show equivalent activity but improved solubility and/or solubilization. However, such methods of identification (involving, e.g., design, synthesis, and characterization of salt/polymorphic forms of a drug candidate) are generally time consuming, tedious and are by themselves bottlenecks in getting a new drug to market.

BRIEF SUMMARY OF EMBODIMENTS OF THE INVENTION

One or more embodiments of the invention are directed to an apparatus for evaluating physicochemical properties of sample materials contained in an array of vessels. The apparatus comprises: a light detector; a light source for transmitting a light beam through the sample material in a vessel to the light detector; an analyzer for processing data from the light detector to determine concentration-related properties of the sample material as a function of time; and a mixing system. The mixing system comprises: a plurality of magnetic stirrer elements, each for being placed in a sample material in a different one of the array of vessels; an array of magnetic drive elements, each said magnetic drive element associated with a different one of the array of vessels and being magnetically coupled with a magnetic stirrer element in an associated vessel; and a drive mechanism coupled to the array of magnetic drive elements for simultaneously moving each of the magnetic drive elements relative to an associated vessel to cause corresponding movement of the magnetic stirrer element in the associated vessel to stir the sample material. The array of magnetic drive elements and the drive mechanism are configured to enable passage of the light beam from the light source through the sample material in each vessel to the light detector such that a concentration-related property of the sample material contained in a vessel can be detected as a function of time while the sample material is being stirred by a magnetic stirrer element.

One or more embodiments of the invention are directed to method of evaluating properties of sample materials contained as solutions of unknown concentration in an array of vessels. The method comprises: simultaneously stirring the sample material in each of the array of vessels; and measuring a concentration-related property of a sample material contained in one of the array of vessels in situ as a function of time without invasive insertion of probes in the sample material while the sample materials are being stirred.

One or more embodiments of the invention are directed to a mixing system for use in an apparatus for evaluating physicochemical properties of sample materials contained in an array of vessels. The apparatus includes a light detector, a light source for transmitting a light beam through the sample material in a vessel to the light detector, and an analyzer for processing data from the light detector to determine concentration-related properties of the sample material as a function of time. The mixing system comprises: a plurality of magnetic stirrer elements, each for being placed in a sample material in a different one of the array of vessels; an array of magnetic drive elements, each associated with a different one of the array of vessels and being magnetically coupled with a magnetic stirrer element in an associated vessel; and a drive mechanism coupled to the array of magnetic drive elements for simultaneously moving each of the magnetic drive elements relative to an associated vessel to cause corresponding movement of the magnetic stirrer element in the associated vessel to stir the sample material. The array of magnetic drive elements and the drive mechanism are configured to enable passage of the light beam from the light source through the sample material in each vessel to the light detector such that a concentration-related property of the sample material contained in a vessel can be detected as a function of time while the sample material is being stirred by a magnetic stirrer element.

Various embodiments of the invention are provided in the following detailed description. As will be realized, the invention is capable of other and different embodiments, and its several details may be capable of modifications in various respects, all without departing from the invention. Accordingly, the drawings and description are to be regarded as illustrative in nature and not in a restrictive or limiting sense, with the scope of the application being indicated in the claims.

BRIEF DESCRIPTION OF THE DRAWINGS

FIGS. 1a and 1b illustrate the analytical device and fluidics-potentiometer device enclosures, as separate units and as an integrated unit, respectively.

FIGS. 14a-14c are perspective views of a dual-compartment permeation cell in accordance with one or more embodiments of the invention shown with a light source at the bottom part of the figures producing a collimated beam of light, which shines through the underside of the upper (receiver) vessel of a permeation cell and emerges above the vessel, and directed into a focusing lens unit of the analytical unit in the upper part of the figure. The lower (donor) vessel has an opening for the light to shine through.

DETAILED DESCRIPTION

Figure 1B:
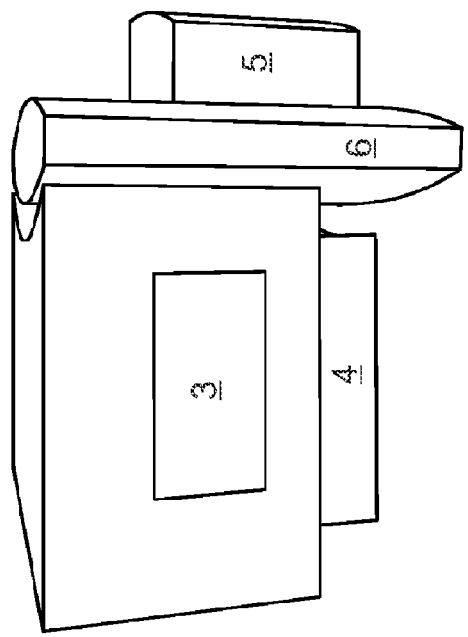
FIGS. 1a and 1b are perspective views of a testing apparatus including an analytical device and a fluidics-potentiometer device in accordance with one or more embodiments of the invention.

Briefly and as will be described in further detail below, with respect to dissolution, precipitation, solubility, or permeability characterization, one or more embodiments of the present invention are directed to improved systems and methods for high-throughput, noninvasive ('noninvasive' herein meaning that no probe of an analytical device used to determine concentration of compound is physically inserted into the solution being tested), and nearly continuous in situ measurement of the release of a compound from a dosage form—and to the measurement of solubility of the compound if given enough compound and enough time for the solution to reach saturation—comprising miniaturized one- or two-dimensional array of vessels filled with dissolution media and using an analytical device to measure the amount of compound released at a given time and comprising a ferromagnetic (hereafter referred to as magnetic) mixing device and comprising a device for maintaining generally constant temperature and comprising a device to inhibit evaporation of dissolution media. The compound may be introduced as a powder, or as one or a few crystalline/amorphous particles, or as a compressed pellet of easily determined exposed surface area (needed for the traditional intrinsic dissolution rate, IDR, measurement), or as an aliquot of concentrated stock solution (for measurement of solubility by precipitation), or any of the aforementioned forms plus a formulation ingredient (also herein called an excipient) or a combination of ingredients. The dissolution solvent media may comprise water, aqueous buffer, single or multiple formulation ingredients (including cosolvents), and, during the concentration measurement, may contain suspended particles of undissolved compound or of undissolved formulation ingredients. One or more additional embodiments of the invention are directed to systems for determining a dissolution profile for a sample compound. The process of precipitation measurement uses generally the same approach as described above when precipitation follows polymorphic transformation of the original form of the abovementioned solid. In addition, precipitation may be initiated from a supersaturated solution containing the test compound.

Briefly and as will be described in further detail below, with respect to membrane permeability characterization, one or more embodiments of the present invention are directed to improved systems for high-throughput, noninvasive, and nearly continuous in situ measurement of concentration of a compound after its transport across the membrane barrier, comprising two miniaturized one- or two-dimensional arrays of vessels, one array placed above the other, to form a "sandwich" of two arrays of vessels. In one preferred embodiment for noncellular permeability measurement (NCPM), (a) the bottom array of vessel, herein referred to as the donor array of vessels for NCPM, is filled with a medium into which the chemical compound is placed, and (b) the top array of vessels, herein referred to as the receiver array of vessels for NCPM, is filled with a medium into which the compound is transported during the permeation period. In another preferred embodiment for cellular permeability measurement (CPM), (a) the top array of vessel, herein referred to as the donor array of vessels for CPM, is filled with a medium into which the chemical compound is placed, and (b) the bottom array of vessels, herein referred to as the receiver array of vessels for CPM, is filled with a medium into which the compound is transported during the permeation period. When combined, each donor-receiver vessel pair in the dual array of vessels constitutes a two-compartment permeation cell, the two vessels separated by a permeability barrier supported by a porous microfilter, which may comprise a monolayer of cultured cells (CPM), or a biomimetic artificial membrane barrier (NCPM, e.g., PAMPA, etc.), separating a solution of a test compound from a solution initially free of it. The analytical device noninvasively and in situ measures the amount of compound that appears in the receiver vessel at a given time during the permeation period. Each vessel in the two stacked arrays contains a magnetic stirrer element and optionally is connected to a device for maintaining generally constant temperature and is covered by a device to inhibit evaporation of the media. In the preferred embodiment for permeability measurement, the compound-containing donor solution is prepared externally and inserted into the analytical device, but in some other embodiments, the compound may be may be added to a medium as a powder, or as one or a few crystalline/amorphous particles, or as an aliquot of concentrated stock solution (e.g., as 10 mM DMSO solution of compound), or any of the aforementioned forms plus an excipient or a combination of excipients. The permeation solvent media may comprise water, aqueous buffer, single or multiple formulation ingredients (including cosolvents), and, during the concentration measurement, may contain suspended particles of undissolved compound or of undissolved formulation ingredients. One or more further embodiments of the invention are directed to systems for determining a permeability profile for a sample compound, indicating the increase in concentration of the compound entering the receiver vessel during the permeation time.

One or more embodiments of the present invention are directed to noninvasive in situ methods utilizing spectroscopic concentration determination systems to evaluate and study the dissolution, precipitation, solubility, and permeability characteristics of compounds or compound formulations and particularly of drug candidates or drug candidate formulations. One or more embodiments of the present invention particularly relate to detection systems for measuring dissolution, precipitation, solubility, and permeability characteristics of dosage forms using ultraviolet/visible (UV/Vis), infrared (IR), near-IR, or fluorescence spectroscopy techniques, singularly or in combinations (e.g., UV/Vis-fluorescence).

One or more embodiments of the present invention are directed to improved systems of agitation of the compound-containing medium, agitation comprising a rotating or oscillating magnetic device located outside the arrays of vessels, magnetically coupled to the magnetic stirrer elements inside each vessel, and further coupled in action to the analytical device so as to limit interference to noninvasive and in situ concentration measurement.

One or more embodiments of the present invention are directed to improved miniaturized one- or two-dimensional array of sample vessels comprising designs accommodating a magnetic stirrer element and compound samples in the forms of powder, one or a few crystalline/amorphous particles, compressed pellet (when measuring IDR), or an aliquot of concentrated stock solution added to a medium.

One or more embodiments of the present invention are directed to improved methods and devices for inhibiting sample solution evaporation and liquid surface distortions due to the meniscus effects during the dissolution, precipitation, solubility, or permeability evaluation, without interfering with the noninvasive in situ concentration measurement during agitation of the compound containing medium.

One or more embodiments of the present invention are directed to a system for automated dispensing of small volume of dissolution media and the automated adjustment of the properties of the media, such as pH and ionic strength. A miniaturized micro pH electrode can be used to confirm pH of solutions and to establish a near-linear volume-pH relationship from the "titration" of a universal buffer solution, comprising a process of additions of mineral acid or base "titrant" to a solution containing several ionizable compounds, followed by readings of pH, the ionizable compounds selected to produce a near-linear plot of pH vs. volume of titrant. This system comprises a solution reservoir for containing a liquid test medium or pH adjustment solution or ionic strength adjustment solution and an automated liquid handing system comprising a dispensing probe, a holder arm for translating the dispensing probe, and a pump in continuous or selectable fluid communication with the dispensing probe for providing a motive force at least for dispensing a portion of the liquid media into the probe to effect dispensing. The dispensing probes are preferably under separate functional control from each other (allowing for independent dispensing), but may be structurally integrated through a common probe head, allowing for integrated positional control of the dispensing.

Methods and systems in accordance with various embodiments of the invention can provide reliable, reproducible, high-throughput, dissolution, precipitation, solubility, and permeability testing that only require a small amount of sample compound for testing or screening, where concentration measurement can be performed noninvasively and in situ, eliminating the need for mechanical sampling of assay media, and filtration/centrifugation of the sampled aliquot.

In one or more embodiments of such methods and systems for determining a physicochemical characteristic, not more than about 5 mg of compound is compressed into a pellet and is combined with not more than 3 mL of a solvent, or preferably not more than about 1 mg of compound in powder form is combined with not more than 1 mL of a solvent, or preferably not more than about 0.01 mg of one or a few crystalline/amorphous particles of compound are combined with not more than 0.2 mL of a solvent. At least a portion of the sample compound is dissolved in the solvent over a period of time to form a solution, with the period of time defining a dissolution period. The assay solution has a concentration of the sample compound that varies during the dissolution/precipitation/permeation period. The concentration of the sample compound is determined at periods of time well below 1 s (one second) per sample solution, to effect the collection of at least 30-100 concentrations over the dissolution/precipitation/permeation time per sample solution. The actual time interval between successive measurements in any particular vessel depends on the total number of vessels in the array. The invention does not preclude the use of more than 5 mg of test compound: in instances where the test compound is relatively soluble, a provision is available to make a thicker pellet, using more than 5 mg of compound.

One or more embodiments of the present invention are directed to methods for generating data defining a dissolution/precipitation/permeation profile for a sample compound. According to these methods, a dissolution/precipitation/permeation profile is determined by any of the methods described in connection with the aforementioned embodiments, and the resulting data can be a data set that is preferably represented on a graphical user interface in graphical or tabular form in real time.

One or more embodiments of the present invention are directed to improved methods for predicting the dissolution/precipitation/permeability profile provided by a controlled release/permeation of compound comprising taking noninvasive and nearly continuous in situ measurements of the amount of compound released/transported for a portion of the time over which the compound is expected to be released/transported and predicting the remainder of the dissolution/precipitation/permeability curve based on the values obtained.

Embodiments of the present invention provide several advantages, particularly in connection with dissolution, precipitation, solubility, and permeability measurement of small amounts sample compounds. Embodiments of the invention are useful in many fields, including without limitation in characterization of compounds in high-throughput workflows. In a preferred application, embodiments of the invention can be advantageously applied for noninvasive and in situ evaluating dissolution, precipitation, solubility, and permeability characteristics of drug candidates or drug candidate compositions.

Embodiments of the present invention also provide several advantages in connection with noninvasive and in situ parallel measurement of concentration of compounds in high-throughput tests, such as cellular (both epithelial and endothelial) and noncellular (e.g., PAMPA, etc.) permeability assays, model blood-brain barrier (BBB) permeability assays, stability assays, and the like.

One or more embodiments of the present invention are directed to a system for the assessment of the effect of excipients on the predicted absorption potential of low solubility compounds comprising monitoring the change in concentration of the studied compounds appearing in the receiver vessel of a dual array of vessels permeation system, the dual arrays of vessels separated by membrane barriers, while varying the excipient components (type and/or concentration) in the donor array of vessels. The barriers can constitute an artificial membrane (e.g., a filter impregnated with a lipophilic solution, i.e., the PAMPA model), cultured endothelial cells (e.g., RBE4), or other cultured cell models (e.g., Caco-2, MDCK, etc.).

DESCRIPTION OF EMBODIMENTS

Briefly, in accordance with one or more embodiments of the invention, methods and systems are provided for determining a dissolution/precipitation/permeability profile and the solubility of a sample compound or of multiple sample compounds that are, e.g., members of an array or library. In accordance with one or more embodiments of the invention, methods are provided for generating data, such as a data set, for defining a dissolution/precipitation/permeability profile of a sample compound or of multiple sample compounds that are members of an array or library.

Methods for Determining a Dissolution Profile

One or more embodiments of the invention are directed to methods for determining a dissolution profile and/or solubility of a sample compound, or of multiple sample compounds that are, e.g., members of an array or library. The methods generally comprise (i) dissolving at least a portion of the sample compound in the solvent over a period of time to form a solution, where the period of time defines a dissolution period, and the solution has a concentration of the sample compound that varies during the dissolution period, and reaches a time-independent value of solubility if allowed enough compound and enough time to dissolve to reach saturation; (ii) agitating the solution during the dissolution period so that undissolved compound particulates or particulate constituents of the medium are generally uniformly suspended; (iii) in situ (effectively in real time) analyzing the dissolving suspension in the solution to determine the concentration of the sample compound in the solution, without invasive mechanical sampling and filtration/centrifugation; (iv) the dissolving preferably initiated by combining an amount of the sample compound with an amount of a liquid media (e.g., a solvent) into which the sample compound will dissolve; (v) inhibiting evaporation while maintaining a generally constant temperature; (vi) suppressing liquid surface distortions due to the meniscus effect; (vii) predicting the remainder of the dissolution curve on the values obtained within the dissolution period; (viii) displaying the dissolution profile, both in real time and forward predicted, and displaying in a graphic symbol the proportion of compound dissolved in real time.

These methods particularly include one or more of the following features, considered alone or in combination in every possible permutation.

(I) the type of sample compound (e.g., drug candidate); (II) the relatively small amount (e.g., weight) of the sample compound (e.g., not more than about 5 mg, and preferably not more than 0.01 mg); (III) the relatively small amount (e.g., volume) of the medium (e.g., solvent) with which the sample compound is combined to initiate dissolution (e.g., not more than about 3 mL, and preferably not more than 0.2 mL); (IV) the relatively small one- or two-dimensional array of sample vessels and the fast noninvasive in situ concentration measurement systems, acquiring data at, e.g., <1 second per sample solution vessel, advantageously circumventing mechanical sampling and/or filtration/centrifugation; (V) the protocols (including specific methods and/or devices) for maintaining a dispersion formed by combining a solid sample compound with a solvent, the dispersion comprising the solution being sampled and the undissolved solid sample compound or undissolved particulate constituents of the medium dispersed in the solution (e.g., through agitation); (VI) the protocols (including specific methods and/or devices) by which these methods can be used to obtain a dissolution profile that is representative of dissolution in a dynamic environment, such as would mimic the environment along various regions of the gastrointestinal tract (e.g., by varying, and preferably controllably varying, a property, such as pH or ionic strength, buffer capacity, or ionic constituents of the solvent medium over time); and (VII) the protocols (including specific methods and/or devices) by which these methods can be applied to a high-throughput method for evaluating a library or an array of sample compounds (e.g., a one- or two-dimensional array of sample compounds in vessels formed on or supported by a common substrate).

Because embodiments of the invention are contemplated and described with respect to each and every possible combination and permutation of these enumerated features (I-VII), a person of skill in the art would readily appreciate, e.g., that these methods in accordance with one or more embodiments of the invention can be described by the above-recited general steps (i), (ii) and (iii), and optionally (iv), (v), (vi), (vii), or (viii), in combination with one or more of features I-VII.

Methods for Generating Data for Defining a Dissolution Profile

One or more embodiments of the invention are directed to methods for generating data, such as a data set, for defining a dissolution profile of a sample compound or of multiple sample compounds that are members of an array or library. Generally, such methods comprise the general steps (i), (ii) and (iii), and optionally (iv), (v), (vi), (vii), or (viii), as described above in connection with the methods for determining a dissolution profile of a sample compound (or of multiple sample compounds that are, e.g., members of an array or library), as supplemented herein. Preferably, the generated data, such as a data set, can be retrieved from memory, e.g., for being displayed on a graphical user interface in real time or after data retrieval in high-content "client" reports. Additionally, these methods are also particularly characterized by one or more of the aforementioned features (I-VII), considered alone or in combination in every possible permutation, with preferred and permutations as described above.

Systems for Determining a Dissolution Profile

In accordance with one or more embodiments of the invention, systems are provided for determining a dissolution profile of a sample compound or of multiple sample compounds that are, e.g., members of an array or library. These systems generally comprise (a) a one- or two-dimensional array of sample vessels for dissolving at least a portion of the sample compound in a solvent over a dissolution period of time to form a solution that has a concentration of the sample compound that varies during the dissolution period, (b) a device for agitating the solution so that undissolved compound particulates or particulate constituents of the medium are generally uniformly suspended, (c) an analytical device for determining the concentration of the sample compound in situ and noninvasively, without insertion of detector probes (e.g., fiber optic probes, etc.) into the test medium, and without external mechanical sampling and filtration/centrifugation, (d) a device for maintaining generally constant temperature in the vessel, (e) a device for inhibiting evaporation, and (f) a device for suppressing solution surface distortions due to meniscus effects. Generally, such systems preferably also include a microprocessor, most preferably together with automation software for controlling the dispensing probe, and a control system and software for controlling the analytical device.

Additionally, these systems can also include one or more of features I and II (with respect to defining a fill level of a vessel or a vessel maximum fill volume), and/or by one or more of the features IV and V, as described generally above and in more detail below. These systems are further particularly characterized by a control system (including software) effective for implementing one or more of the aforementioned feature VII. Such features form a part of the systems in accordance with various embodiments of the invention considered alone or in combination in every possible permutation, with preferred combinations and permutations as described above.

Methods for Determining a Permeability Profile

Another aspect of the invention is directed toward methods for determining a permeability profile of a sample compound, or of multiple sample compounds that are, e.g., members of an array or library. These methods generally comprise (ix) placing a solution of a compound into the donor vessel of a dual-vessel permeation cell, and placing a solution free of sample compound into the receiver vessel of the permeation cell, so that the transport of at least a portion of the sample compound takes place (across the membrane barrier separating the donor and receiver solutions) over a period of time, where the period of time defines a permeation period, and the receiver solution has a concentration of the sample compound that varies during the permeation period, and reaches a time-independent value of concentration if allowed enough time to permeate to reach trans-membrane equilibrium; (x) agitating the solution during the permeation period so that the membrane permeability is not predominantly limited by the aqueous boundary layer resistance; (xi) in situ determining the concentration of the compound in the receiver or donor solution to determine the permeability characteristics, without invasive insertion of detector probes in the test solution, and without invasive mechanical sampling and filtration/centrifugation; (xii) inhibiting evaporation while maintaining generally constant temperature; (xiii) suppressing liquid surface distortions due to the meniscus effect; (xiv) predicting the remainder of the permeation curve on the values obtained within the permeation period; (xv) displaying the permeation profile, both in real time and forward predicted, and displaying in a graphic symbol the proportion of compound transported in real time.

These methods can include one or more of the following features, considered alone or in combination in every possible permutation. Generally considered, the features include the features I-III, as well as: (VIII) the relatively small one- or two-dimensional dual arrays of sample vessels, one serving as the donor array and the other serving as the receiver array, and the fast noninvasive in situ concentration measurement systems, acquiring data at, e.g., <1 second per sample solution vessel, advantageously circumventing mechanical sampling and/or filtration/centrifugation; (IX) the protocols (including specific methods and/or devices) for controllably varying/reducing the effect of the aqueous boundary layer resistance (e.g., through agitation); (X) the protocols (including specific methods and/or devices) by which these methods can be used to obtain a permeation profile that is representative of transport in a dynamic environment, such as would mimic the environment along various regions of the gastrointestinal tract (e.g., by varying, and preferably controllably varying, a property, such as pH or ionic strength, buffer capacity, or ionic constituents of the solvent medium over time); and (XI) the protocols (including specific methods and/or devices) by which these methods can be applied to a high-throughput method for evaluating a library or an array of sample compounds (e.g., a one- or two-dimensional array of sample compounds in vessels formed on or supported by a common substrate).

Because various embodiments of the invention are contemplated and defined with respect to each and every possible combination and permutation of the features (I-III, VIII-XI), a person of skill in the art would readily appreciate, e.g., that these methods can be defined by the above-recited general steps (ix), (x) and (xi), and optionally (xii), (xiii), (xiv), or (xv), in combination with one or more of features I-III, VIII-XI.

Methods for Generating Data for Defining a Permeability Profile

One or more embodiments of the invention are directed to methods for generating data, such as a data set, for defining a permeability profile of a sample compound or of multiple sample compounds that are members of an array or library. Generally, such methods include the general steps (ix), (x) and (xi), and optionally (xii), (xiii), (xiv), or (xv), as described above in connection with the methods for determining a permeability profile of a sample compound (or of multiple sample compounds, e.g., that are members of an array or library), as supplemented herein. Preferably, the generated data, such as a data set, can be retrieved from memory, e.g., for being displayed on a graphical user interface in real time or after data retrieval in high-content "client" reports. Additionally, these methods are also particularly characterized by one or of the aforementioned features (I-III, VIII-XI), considered alone or in combination in every possible permutation, with preferred and permutations as described above.

Systems for Determining a Dissolution Profile

One or more embodiments of the invention are directed to systems for determining a dissolution profile of a sample compound or of multiple sample compounds that are, e.g., members of an array or library. These systems generally include (a) a one- or two-dimensional array of sample vessels for dissolving at least a portion of the sample compound in a solvent over a dissolution period of time to form a solution that has a concentration of the sample compound that varies during the dissolution period, (b) a device for agitating the solution so that undissolved compound particulates or particulate constituents of the medium are uniformly suspended, (c) an analytical device for determining the concentration of the sample compound in situ and noninvasively, without insertion of detector probes into the test solution, and without external mechanical sampling and filtration/centrifugation, (d) a device for maintaining generally constant temperature in the vessel, (e) a device for inhibiting evaporation, and (f) a device for suppressing solution surface distortions due to meniscus effects. Generally, such systems preferably also comprise a microprocessor, most preferably together with automation software for controlling the analytical device.

Additionally, these systems are also particularly characterized by one or more of features I and II (with respect to defining a fill level of a vessel or a vessel maximum fill volume), and/or by one or more of the features IV and V, as described generally above and in more detail below. These systems are further particularly characterized by a control system (including software) effective for implementing one or more of the aforementioned feature VII. Such features describe systems in accordance with various embodiments of the invention considered alone or in combination in every possible permutation, with preferred combinations and permutations as described above.

Systems for Determining a Permeation Profile

One or more embodiments of the invention are directed to systems for determining a permeation profile of a sample compound or of multiple sample compounds that are, e.g., members of an array or library. These systems generally include (a) a one- or two-dimensional array of donor vessels, (b) a matching one- or two-dimension array of receiver vessels, (c) a device for agitating the solution so that the aqueous boundary layer does not pose the predominant resistance to transport of the test compound, (d) an analytical device for determining the concentration of the sample compound in situ and noninvasively, without insertion of detector probes into the test solution, and without external mechanical sampling and filtration/centrifugation, (e) an device for maintaining generally constant temperature in the arrays of vessels, (f) a device for inhibiting evaporation, and (g) a device for suppressing solution surface distortions due to meniscus effects. Generally, such systems preferably also comprise a microprocessor, most preferably together with automation software for controlling the analytical device.

Additionally, these systems are also particularly characterized by one or more of features I and II (with respect to defining a fill level of a vessel or a vessel maximum fill volume), and/or by one or more of the features XIII and IX, as described generally above and in more detail below. These systems are further particularly characterized by a control system (including software) effective for implementing one or more of the aforementioned feature XI. Such features describe systems in accordance with various embodiments of the invention considered alone or in combination in every possible permutation, with preferred combinations and permutations as described above.

Systems for Automated Dispensing of Small Volume Liquid Samples

One or more embodiments of the invention are directed to systems for automated dispensing of small-volume liquid samples, or of multiple liquid samples that are, e.g., members of an array or library. These systems generally include (a) a sample container for containing a liquid sample, (b) an automated liquid handing system comprising a dispensing probe, a holder arm for translating the dispensing probe, and a pump in fluid communication with the dispensing probe for providing a motive force.

Additionally, these systems are also particularly characterized by one or more of features I and II (with respect to defining a fill level of a vessel or a vessel maximum fill volume), as described generally above and in more detail below. These systems are further particularly characterized by a control system (including software) effective for implementing one or more of the aforementioned features VI and VII. Such features describe systems in accordance with various embodiments of the invention considered alone or in combination in every permutation, with preferred combinations and permutations as described herein.

Such systems can be employed in a number of applications for which it is desirable to enjoy the advantages of various embodiments of the present invention, especially in connection with automated dispensing of small-volume liquid samples, or of multiple small-volume liquid samples that are members of an array or library. For example, one could apply this system for evaluating compound stability and/or excipient compatibility of drug candidates, especially in drug compositions, or compound permeability across in vitro cellular or noncellular models of the blood-brain barrier.

System for Automatic Preparation of Solution Buffers

One or more embodiments of the invention are directed to systems for automated dispensing of small-volume aliquots of a standardized solution (e.g., 0.1 to 1.0 mole/liter in concentration) of a mineral acid (e.g., HCl) or base (e.g., NaOH) into vessels in an array of vessels containing a universal buffer medium delivered by the aforementioned system. The small-volume aliquot of mineral acid or base (herein known as titrant) to produce a buffer of desired pH is determined from a separate standardization of the titrant against a known volume of the universal buffer contained in one of the vessels of the array of vessels, with pH measured during the titration operation by a miniaturized pH electrode, such as the Ross® brand available from Thermo (Beverley, Mass., USA). The buffer preparation systems generally include (a) a sample container for containing a standardized mineral acid or base solution, (b) a sample container for containing a universal buffer solution, such as the Prisma™ brand universal buffer solution available from pION (Woburn, Mass., USA), and (c) an automated liquid handing system comprising a dispensing probe, a robotic arm for translating the dispensing probe, and a pump in fluid communication with the dispensing probe for providing a motive force.

Sample Compounds

As used herein, a sample refers to a single, discrete, individual unit of a compound that is being evaluated. The sample compound is a compound or composition being evaluated or tested or screened, for which a time variation in a property thereof is being determined, including for example in a preferred application, for which the dissolution/precipitation/permeability profile is to be determined. The sample compound can comprise or consist essentially of an organic compound, an inorganic compound, a metal-containing organic compound, or a combination thereof. The sample compound can comprise or consist essentially of a polymer (e.g., a biological polymer or a non-biological polymer), or a composite compound.

Preferred organic compounds include small organic compounds (e.g., pharmaceuticals, agrochemicals, environmental pollutants, etc.) or biological polymers (e.g., nucleic acid polymers such as oligonucleotides, deoxyribonucleic acid polymers (DNA), ribonucleic acid polymers (RNA), etc., and amino acid polymers such as peptides, proteins, enzymes, etc.).

In some preferred embodiments, the sample compound is a drug sample. A drug sample refers to a sample that is a drug candidate, a combination of drug candidates, or a drug composition. A drug composition refers to a composition that has one or more drug candidates and at least one excipient. Hence, the sample compound preferably comprises or consists essentially of a drug candidate. A drug candidate is a compound (salt or neutral) shown in one or more various assays to have pharmacological (prophylactic or therapeutic) activity. A drug candidate may also be, but has not necessarily been, shown to be safe under various toxicity assays. An active pharmaceutical ingredient (API) is a specific compound (salt or neutral), typically that has been approved by a governmental entity for use in a pharmaceutical, e.g., has been demonstrated to be, and is typically approved by a governmental entity (e.g., U.S. Food and Drug Administration) to be safe and effective for a particular indication. The methods and systems described in this patent application are preferred for use in evaluating sample compounds that are drug candidates, which may or may not be APIs. Moreover, as those skilled in the art will appreciate, the exact API or drug candidate is not critical to this invention, but is typically a small organic molecule. In some cases, the drug candidate or API can be a biological polymer such as an oligonucleotide, a DNA, a RNA, a polypeptide or a protein. Some drug candidates have salts that are anionic or cationic and some drug candidates are neutrals. No matter the form, drug candidates may have different crystallographic polymorphs. Herein, the term polymorph is intended to include polymorphs, pseudopolymorphs, hydrates, solvates and the like. The term excipient refers to a drug composition component that is typically intended to aid in manufacture, administration, absorption, appearance enhancement or retention of quality of a drug. Excipients can initiate, propagate or participate in chemical or physical interactions with a drug candidate, possibly leading to compromised or enhanced quality or performance of the drug. One example of an excipient that is commonly used is a solvent. For example, solvents may have an effect on the reaction rate of a drug candidate, or the degradation rate of a drug may change with the dielectric constant or ionic strength of the medium. One or more excipients used together with one or more drug candidates in a drug composition, can have a significant effect on dissolution/precipitation/permeability of a drug composition sample compound, and therefore, on the bioavailability of such drug sample. Another example of an excipient stems from nanotechnology, in the form of nanomaterials designed to facilitate bio-delivery of poorly absorbable drug candidates.

The particular physical state or form of the compound is not narrowly critical to the invention. The sample compound, such as a drug or a drug composition, can take any form, such as a liquid, a solid, a gel, a nanoparticle, and the like. In preferred embodiments, the sample compound is in the form of a solid, such as a crystalline solid. Crystalline solids can be single crystals or polycrystalline. The sample compound can, in some embodiments, be provided for evaluation already in a partially dissolved state, including, e.g., as a suspension or dispersion (including both uniform and non-uniform dispersions), or as a solid-liquid emulsion. A dispersion, e.g., can comprise a partially dissolved solid sample compound dispersed in a solution, i.e., dispersed in a liquid media into which the solid sample compound is dissolving. In preferred embodiments, the sample compound is provided as a dispersion, or is provided as a solid and combined with a solvent to form a uniform dispersion.

In some preferred embodiments of the dissolution methods and systems, the compound may be pressed in a die into a small disk of easily measurable exposed surface area, a parameter needed for traditional intrinsic dissolution rate (IDR) measurement.

Amounts of Sample Compound

The amount of sample compound being evaluated or tested or screened is not critical to many embodiments of the invention, but as noted above, various embodiments of the invention offer particular advantages with respect to methods and systems for evaluating or testing or screening relatively small amounts (e.g., weight) of sample compounds. Hence, in preferred embodiments, the amount of sample compound provided to a sample vessel is preferably not more than about 5 mg, more preferably not more than about 1 mg. Also, for some applications, such as for high-throughput screening of formulations such as drug compositions, the amount of sample compound can be characterized as being not more than about 100 µg (0.1 mg), or not more than about 10 µg (0.01 mg) or not more than about 1 µg (0.001 mg).

Amounts of Solvent

The solvent generally refers to the liquid medium into which the sample compound is dissolved during the physico-chemical property assessment. The particular type of liquid medium used in connection with the methods of this invention is not narrowly critical, and can be selected based on the type of sample compound being investigated. Generally, the liquid media can be a solvent having a single unitary chemical composition (e.g., substantially pure solvents consisting essentially of one type of solvent, such as water, ethanol, etc.) or can be a solvent having a combination of chemical compositions (e.g., cosolvents comprising two or more miscible or immiscible solvents, such as water/ethanol cosolvents). The solvent can generally include one or component agents for controlling pH, buffer capacity, or ionic strength (e.g., different salts), or one or more agents or components that are solubilizers, disintegrants, or surfactants, or nanoparticle adsorbents.

In some preferred applications, such as applications for evaluating dissolution/precipitation/permeability of drug candidates, the liquid medium can be water or a medium, such as a buffered aqueous medium, including without limitation buffered solutions having a pH ranging from about 2 to about 10. The liquid medium used as the solvent can also be biological fluids (e.g., blood, saliva, gastric fluid, human intestinal fluid), or mimics of such fluids (e.g., simulated intestinal fluids, simulated gastric fluid, artificial blood or artificial saliva, or artificial membrane permeability barriers, etc.).

The amount of solvent combined with the sample compound in the sample vessel for evaluation is not critical to many embodiments of the invention. Generally, the sample compound is combined with an amount of solvent effective for forming a solution having a detectable concentration of sample compound in the solution. As such, a person skilled in the art will appreciate that the amount of solvent to be combined with the sample compound can be determined based on the type of sample compound, the amount of the sample compound, and the sensitivity of the analytical device or concentration measurement system.

In some preferred applications, such as applications for evaluating physicochemical properties of drug candidates, the sample compound is combined with an amount of solvent effective for forming a solution having a concentration of sample compound in the solution ranging from about 0.001 mg/mL to about 30 mg/mL, preferably from about 0.05 mg/mL to about 5 mg/mL. As non-limiting examples, the sample compound (e.g., a drug candidate-containing sample) can be combined with a solvent with the following relative amounts: not more than about 5 mg of sample compound with not more than about 3 mL of solvent; not more than about 1 mg of sample compound with not more than about 1 mL of solvent; and not more than about 0.01 mg of sample compound with not more than about 0.1 mL of solvent.

As noted above, various embodiments of the invention offer particular advantages with respect to methods and systems for evaluating or testing or screening relatively small amounts (e.g., weight) of sample compounds, and also for evaluating such sample compounds in relative small volumes of solution. Hence, in preferred embodiments, the total amount of solvent to be combined with the sample compound in each sample vessel and correspondingly the total amount of the resulting solution, e.g., of a dispersion comprising the solution and undissolved solid sample compound that is formed from the combination of a solvent and a solid sample is preferably not more than about 3 mL or not more than about 1 mL, or not more than about 0.1 mL.

Sample Container and In Situ Measurement of Concentration

Dissolution is initiated by combining the sample compound with a solvent, preferably with a suitable solvent, and preferably under conditions (e.g., temperature) effective for causing at least a portion of the sample compound to dissolve in the solvent. The sample compound and solvent can be combined in a vessel such as a sample vessel in a one- or two-dimensional array of such vessels. The order of addition can include adding the solvent to the contained sample compound, or adding the sample compound to the contained solvent.

An array of multiple sample compounds is contained in an array of multiple vessels, respectively, with each sample compound in its own discrete, dedicated vessel. In such cases, the vessels can be structurally integrated, such as being formed in or supported by a common substrate. Hence, e.g., the vessels can be wells of a microtiter plate, or can be individual vials supported in wells of a microtiter plate. Standard microtiter formats (typically having a 9 mm center-to-center distance between adjacent wells or vials—that is, a 9 mm pitch), typically in an 8 row by 12 column (or vice-versa) format, is particular useful for performing high-throughput screening of samples. Another preferred format for larger volume vessels is a twenty-four well plate in a 4×6 format with about a 20 mm pitch (center-to-center distance of adjacent wells or vials). Other microtiter formats can also be employed, including one-dimensional arrays. The vessels can be open during the dissolution process, or can be covered, such as with a cover designed not to interfere with the operation of the analytical device, during the dissolution process, and can be arranged to avoid cross-contamination between adjacent vessels. The vessels can be of any suitable compound, including for example glass, plastic, etc., except that a portion of the horizontal surface should be constructed of material not significantly interfering with the operation of the analytical device. In accordance with one or more embodiments, the array of vessels is a low-UV absorbing material microtiter plate.

The sample compound is combined with the solvent at an initiation time, to initiate dissolution of the sample compound in the solvent. In preferred protocols, the dissolution profile is characterized very early in the dissolution period-to provide valuable information about the kinetics of the initial part of the dissolution process.

The above description details the methodologies by which dissolution is initiated, and by which a dissolution profile is obtained. Such methodologies can be advantageously effected using the system described below in connection with the preferred embodiments of the invention.

Permeation is initiated when an array of donor vessels containing sample solutions is combined with an array of receiver vessels containing just the media to form a "sandwich" array of permeation cells. In other respects, permeation vessel arrays are very similar to those used for dissolution studies, and many of the aforementioned considerations for dissolution apply to permeability measurements.

The automated dispensing probe can be a component of an automated solid (e.g., powder) dispenser, such as the Powderinium (Autodose, S. A., Geneva, Switzerland) or of an automated liquid dispenser, such as the Cavro (Tecan Scientific Instruments, San Jose, Calif., USA). Automated solid dispensers can further comprise a robotic arm for translating the automated dispensing probe for positioning, a hopper or other source container for the compound to be dispensed, and automation software for controlling the dispenser. An automated liquid dispenser can be an automated liquid handling robot that further comprises a robotic arm for translating the automated dispensing probe for positioning, a source container for the solvent or sample compound to be dispensed, a pump in fluid communication with the dispensing probe for providing a motive force for dispensing, e.g., the solvent, into the sample vessel array, and automation software for controlling the dispenser. Further, the automation software for these devices is can be separate, or can be partially or totally integrated.

Agitation and Mixing

As noted, the dissolution profiling methods and systems in accordance with various embodiments of the invention can be particularly advantageous in connection with dispersions comprising a solid sample compound that is partially dissolved in a solvent to form a solution, and that is partially undissolved and dispersed in the solution. Such dispersions (or suspensions) can be agitated or mixed. Such agitation or mixing can help ensure sufficient contact between the undissolved solid sample compounds and the solution during the dissolution period, and can provide a physical averaging of the solutions with respect to the property of interest (e.g., concentration). Such agitation or mixing can also help maintain the dispersion, preferably as a substantially uniform dispersion. Preferably, the dispersion is substantially uniform in that it is free of continuous stratification layers that would be of a thickness that reflects in a change in a bulk property (e.g., optical turbidity, density) of one layer versus another layer.

The contents of the vessel array can be agitated or mixed by magnetic stirring. In particular, such agitation or mixing can be advantageously effected using the system described below in connection with the preferred embodiments of the invention.

The permeability profiling methods and systems in accordance with various embodiments of the present invention benefit from efficient agitation in that the contribution to the total resistance to transport due to that of the aqueous boundary layer is minimized. As is known in the art, in vitro permeability methods not employing some sort of stirring agitation can have aqueous boundary layers as thick as 1000-4000 μm, whereas the aqueous boundary layer in the intestinal tract is estimated to be about 100 μm. In order to execute a biomimetic assay, stirring is highly desirable with in vitro permeability assays.

Since the various embodiments of invention concern noninvasive in situ measurement of concentration, the aforementioned agitation should allow the functioning of the analytical device during the ongoing assay.

Physicochemical Property Profiling Environment: Temperature, Evaporation and Meniscus Effects The physicochemical property profiling environment, including, e.g., the composition of the solution in which the assay takes place occurs during the dissolution/precipitation/permeability period, and/or the temperature or other properties during the period, and/or the temperature and/or humidity and/or other environments to which a sample compound is exposed prior to the period can be controlled, including as a parameter of the evaluation. Temperature is a particularly preferred parameter to control during the period, since solubility, permeability, and solubilization rate can vary as a function of temperature. For example, the protocols (including the methods and systems) in accordance with various embodiments of the invention can be adapted to control the temperature of the solution at a desired temperature or within a desired range of temperatures, typically defined by upper and lower setpoints of a temperature controller. In some applications, for instance, one can control the temperature to be at or near or including ambient or room temperature (e.g., about 25° C.) or at or near or including normal body temperature (e.g., about 37° C.).

The transmission of a light beam near the edges of a vessel may be subject to distortion due to the formation of meniscus between the liquid and the wall of the vessel. By capping the surface of the solution helps to substantially eliminate meniscus distortions, and reduces evaporation of the medium solvent.

Dynamic Physicochemical Property Profiling Environment

The assay environment, such as especially the composition of the solution in which the physicochemical property is assessed during the assay period, and/or the temperature or other properties during said period—can be maintained to be substantially the same, or can be varied, and preferably controllably varied over time during said period. Advantageously, such capabilities can be used to obtain a dissolution/precipitation/permeability profile that is representative of dissolution/precipitation/permeability in a dynamic environment. In one non-limiting example, it may be desirable to mimic the environment along various regions of the gastrointestinal tract. For example, the pH of assayed solution intended to mimic the gastrointestinal tract may be controllably varied from acidic (e.g., representing the stomach at pH ranging from about 1.2 to 3) to neutral (e.g., representing the small intestine at pH ranging from about 5 to 8). Other properties that can be varied, and preferably controllably varied include temperature, ionic strength, ratio of solvent to cosolvent, buffer concentration, solubilizer concentration, disintegrant concentration, surfactant concentration, nanoparticle adsorbent concentration, wetting agents, etc.

Such variation can be effected by adding a liquid-media as a make-up agent, as described above, where the liquid-media is effective for changing one or more of the solution properties over time. Alternatively or supplementally, solid or liquid agents or cosolvents can be added directly to the solutions, e.g., using a dispensing probe as described above.

Analysis

The determined concentration of each of the successive noninvasive in situ measurements, when considered in combination with the corresponding times at which the solution was measured, represents a dissolution/precipitation/permeability profile for the sample compound being assayed. In the case of dissolution, where the surface area of the sample compound is known or determined, the methods can further be used for determining an intrinsic dissolution rate for the sample compound for one or more times during the dissolution period. Alternatively, where the surface area of the sample compound is not known, or where a screening application (comparative evaluation between two or more sample compounds) is desired, such as in high-throughput applications involving an array comprising multiple sample compounds, the method can further comprise comparing the relative dissolution rates for the sample compounds being evaluated for one or more times during the dissolution period.

Analysis can be effected using an analytical device, such as the analytical device described below in connection with the preferred embodiments of the invention. In particular, such analysis can be effected using, e.g., an analytical device comprising a detector, the detector is adapted for detecting a property of the one or more separated components. The detector can be selected from one or more of a fluorescence detector, an infrared detector, and an absorbance detector (e.g., especially a UV/Vis absorbance detector).

In accordance with one or more embodiments, the detector is a photodiode array of elements. In accordance with one or more embodiments, the detector is a charge-coupled device (CCD).

In accordance with one or more embodiments, the analytical device is a parallel multi-channel unit adapted to simultaneously analyze two or more emergent beams of light simultaneously.

Formulation Research with High-Throughput Physicochemical Property Profiling

The aforementioned protocols (including specific methods and/or devices) can be applied to a high-throughput method and system for evaluating a library or an array of sample compounds. An array of vessels is an association of two or more, preferably four or more, most preferably eight or more members, such as sample compounds. The one- or two-dimensional array of vessels can comprise multiple members of sample compounds in vessels formed on or supported by a common substrate. The aforementioned protocols can be effected in connection with each of the plurality of members of the array, generally either sequentially in time (i.e., serially), or simultaneously in time (i.e., in parallel). In addition, it is possible that some steps of the methods are effected serially, while other steps of the methods are effected in parallel (e.g., analysis), in each case as compared between different members of the array of vessels. The members of the array of vessels can be varied from each other in a number of ways, including, e.g., differing with respect to chemical composition, differing with respect to crystalline structure (polymorphs), etc. In some embodiments, the compound samples that are members of an array of vessels will be chemically and physically substantially the same (e.g., have the same chemical composition and same crystalline structure), and the method will comprise creating a different dissolution/precipitation/permeation environment (e.g., different pH, different solvents, different temperatures, different ratios of cosolvents, different concentrations of additives) for each of the members of the array of vessels.

The array of vessels of library members for dissolution/precipitation/permeability screening can be advantageously prepared using high-throughput formulation methods and systems. These can be accomplished, e.g., by using an external formulation workstation.

In dissolution profiling, e.g., formulation by wet and/or dry milling can be used. Such formulation is comprised of dispensing with a liquid handling robot all components such as drug candidates, excipients, stabilizers, surfactants, adsorbents, and the like into an array of vials. If a solvent is used to dispense the components, it can be stripped off either by vacuum or by blowing dry nitrogen directly on the array of vessels. The external formulation process can be controlled by computer to automatically mix specific quantities of compound (e.g., drug candidates, solvents, stabilizers, etc.) to form a compound composition. Automatic control of the formulation workstation enables various embodiments of the present invention to receive several libraries or members for dissolution, precipitation, solubility, or permeability characterization. Moreover, automated control reduces possible errors that can be caused by manual control. In addition, automated control may enable embodiments of the present invention to prepare relatively small sample sizes. This advantageously provides high-throughput preparation and screening of dissolution/precipitation/permeability or solubility of the compound compositions.

After the array of vessels of multiple sample compounds is prepared, it may be screened by the profiling methods in accordance with one or more embodiments of the invention disclosed herein. Specifically, a high-throughput drug solubilization characterization or screening method and system are provided to identify and select the form of a drug candidate having desirable dissolution/precipitation/permeability or solubility properties. This solubilization and/or solubility screening method generally comprises: (1) providing a library comprising a plurality of members (i.e., sample compounds), wherein each said library member comprises a drug candidate; (2) determining a dissolution/precipitation/permeability profile and/or solubility characteristic for each of the plurality of library members for solubilization and/or solubility characteristics using any of the methods detailed in this application for determining a dissolution/precipitation/permeability profile or a solubility characteristic; and (3) comparing the dissolution/precipitation/permeability or solubility for each of the plurality of library members.

The solubilization, solubility, or permeability screening system in accordance with one or more embodiments of the invention generally comprises: (a) a plurality of sample vessels, preferably four or more sample vessels, each for containing one member of the library or array of vessels for evaluation, either separately or structurally integrated; (b) an analytical device that is either a serial single-channel unit, adapted to analyze one sample compound at a time, and a plurality of sample compounds sequentially, or a parallel multi-channel unit-adapted to analyze two or more samples simultaneously; preferably, such a system also includes (c) one or more automated dispensing probes. In one parallel embodiment, the physicochemical property screening system comprises two or more sets of structurally integrated or structurally independent automated probes, each set comprising an automated dispensing probe. Such high-throughput physicochemical property screening can be applied alone or in combination with various other screening methods for evaluating other properties of interest, such as stability, solubility, particle size, permeability, etc. Taken in combination as part of a larger workflow, such screens can systematically enhance the efficiency of the process of drug development. In preferred embodiments, all of the above-described steps of the high-throughput physicochemical property screening methods are automated and controlled by a computer. User interfaces can enable users to input commands to computer via an input device-including any suitable device such as, e.g., a conventional keyboard, a wireless keyboard, a mouse, a touch pad, a trackball, a voice activated console, or any combination of such devices. Input device enables a user to enter commands to perform drug selection, library building, screening, etc. If desired, input device may also enable a user to control the various workstations (e.g., for formulation or for physicochemical property screening). A user may also monitor processes operating on the systems on a display device, such as a computer monitor, a television, a flat panel display, a liquid crystal display, a cathode-ray tube (CRT), or any other suitable display device. Communication paths can be provided and configured to enable to transfer among the computer, the formulation workstation, the physicochemical property screening workstation, and user interfaces.

Preferred Embodiment for High-Throughput Dissolution Monitoring

Figure 1A:
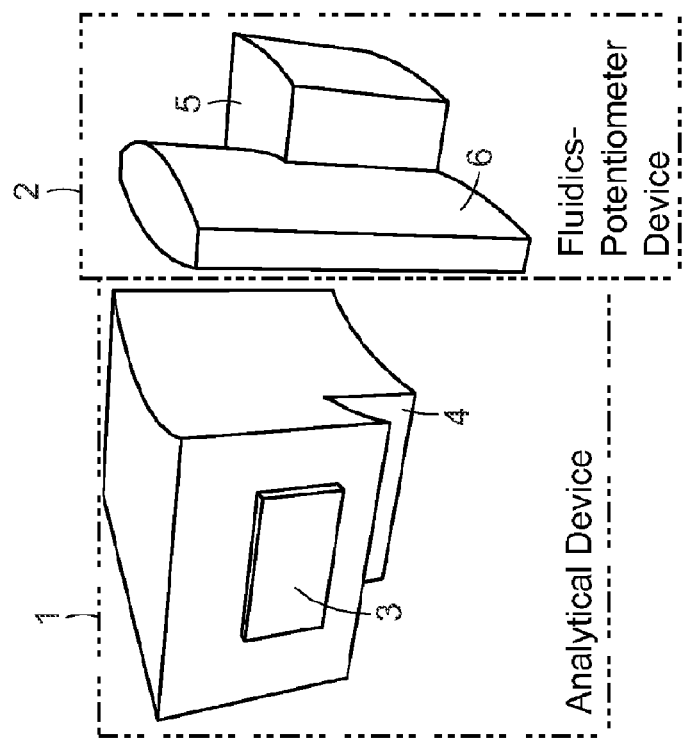
Figure 2:
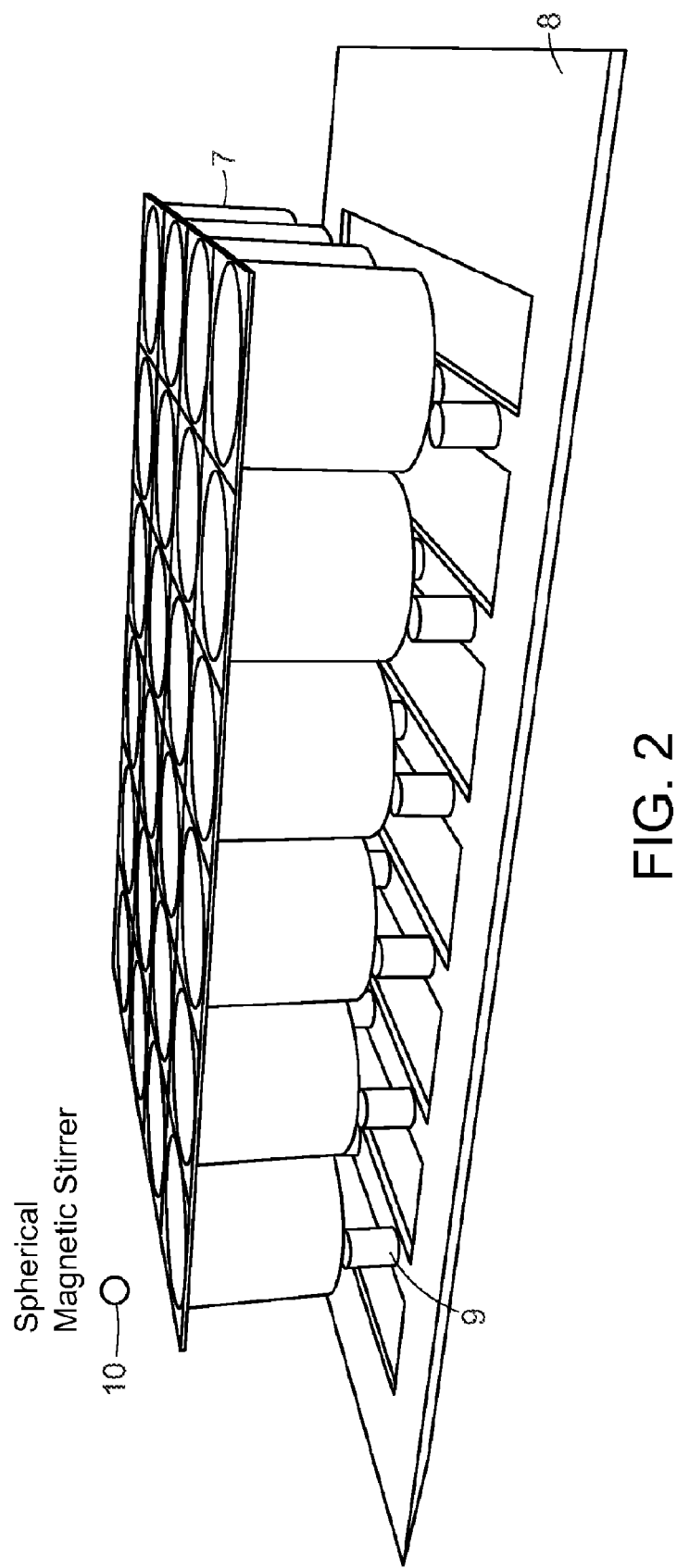
FIG. 2 is a perspective view of a 4×6 array of cylindrical vessels suspended over a 4×6 plate array of magnets, and a spherical magnetic stirrer in accordance with one or more embodiments of the invention.
Figure 3:
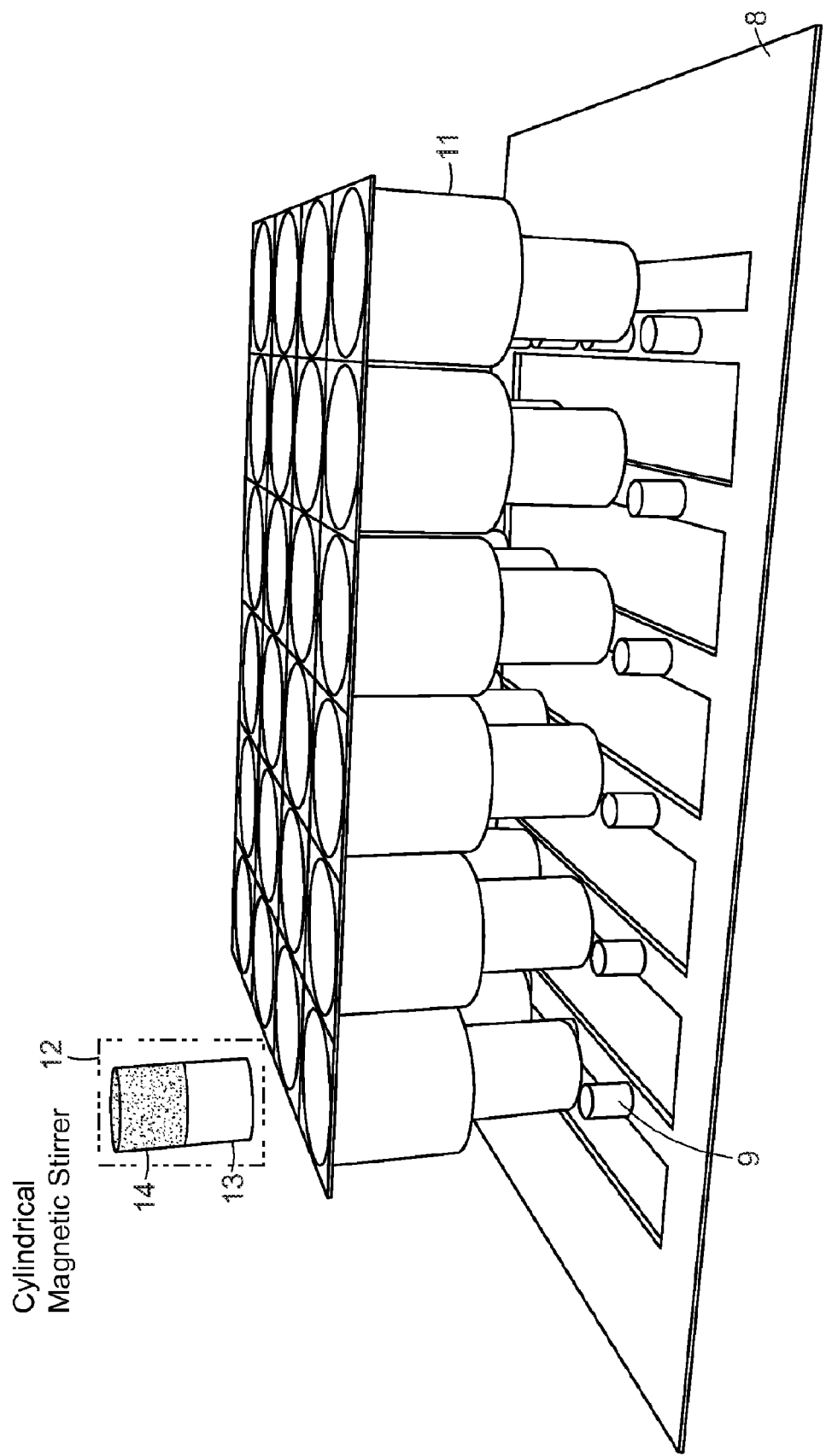
FIG. 3 is a perspective view of a 4×6 array of bicylindrical dual-compartment vessels suspended over a 4×6 plate array of magnets, with one cylindrical magnetic stirrer showing in accordance with one or more embodiments of the invention.

FIG. 1a shows the analytical device 1 and the fluidics-potentiometer device 2 as separated components, and FIG. 1b shows the two devices as a single integrated unit. In high-throughput formulation applications, the fluidics-potentiometer device 2 may be substituted by an enhanced-feature robotic fluidic workstation, such as those available from Tecan (Maennedorf, Switzerland), Beckman Coulter (Fullerton, Calif., USA), and Symyx (Sunnyvale, Calif., USA). In such a robotic configuration, the analytical device 1 can be latched to the robotic workstation, where the overhang space 4 allows for the array of vessels platform 3 to extend into the worktable space accessible to the robotic system, without the need of a special adapter. Platform 3 slides out of analytical device 1 so that an array of vessels can be put in or taken out.

Components of the analytical device 1 include: (i) platform 3, movable in two directions, which transports a number of sub-assemblies (described in the next paragraph), (ii) a xy-position actuator device (not shown in the drawings) for moving platform 3 in a plane, (iii) fixed-position light source 16, (iv) a fixed-position light detector 17, (v) an optional semi-micro/micro double junction combination pH electrode 32 (with signal wire connection to the fluidics-potentiometer device 2), (vi) an optional electrode holder and vertical-motion actuator to lower/raise the electrode in/out of a vessel (not shown in the figures), (vii) optional two or more quartz-capillary tips for fluid delivery and a vertical-motion actuator to lower/raise said tips in/out of a vessel (not shown in the figures), (viii) an optional miniaturized temperature sensor device and vertical-motion actuator to lower/raise the temperature sensor in/out of a vessel (sensor may be attached to one of the tips for fluid delivery—not shown in the figures), and (ix) electronics control circuitry, power supply and cooling fan. In some optional embodiments, there may be an array of light sources 16 and an array of detectors 17 (or a single detector 17 coupled to a multiplex light beam switching unit), to enhance the throughput of the analytical device 1.

In accordance with one or more embodiments of the invention, the light source 16 comprises an ultraviolet-spectrum emitting lamp, a visible-spectrum emitting lamp, a combination ultraviolet-visible lamp, an infrared-spectrum emitting lamp, or a near-infrared-spectrum emitting lamp.

The aforementioned platform 3, carries several sub-assemblies. Platform 3 is translated in a plane by a xy-position actuator, available from, e.g., Precision Alliance (Fort Mill, S.C., USA). The sub-assemblies of platform 3 include a mixing device for stirring the sample materials in the array of vessels 7, 11 as the sample materials are being analyzed by the analytical device 1.

As described in further detail below, the sample materials in the array of vessels 7, 11 are stirred using magnetic stirrer elements, which are placed in the sample materials and are caused to move therein. The mixing device includes an array of magnetic drive elements, each associated with a different one of the array of vessels and being magnetically coupled with a magnetic stirrer element in an associated vessel. A drive mechanism is coupled to the array of magnetic drive elements for simultaneously moving each of the magnetic drive elements relative to an associated vessel to cause corresponding movement of the magnetic stirrer element in the associated vessel to stir the sample material. The array of magnetic drive elements and the drive mechanism are configured to enable passage of the light beam from the light source through the sample material in each vessel to the light detector such that a concentration-related property of the sample material contained in a vessel can be detected as a function of time while the sample material is being stirred by a magnetic stirrer element. Either the magnetic stirrer elements comprise permanent magnets or the magnetic drive elements comprise permanent magnets. Alternatively, both the magnetic stirrer elements and the magnetic drive elements comprise permanent magnets.

Figure 4C:
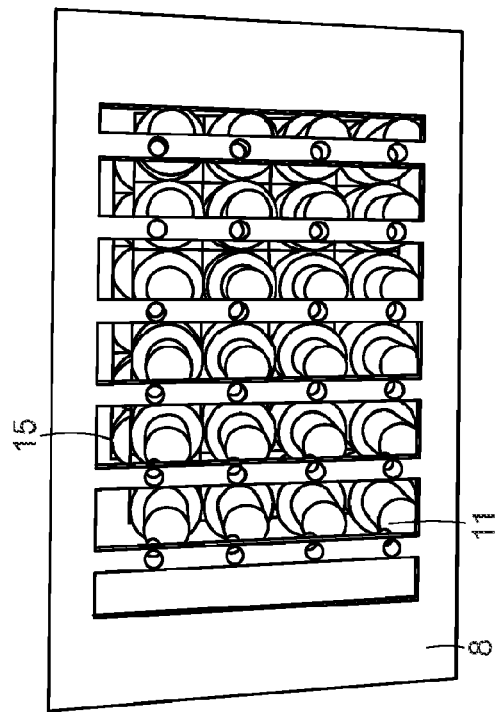
FIGS. 4a-4c are side, top, and bottom perspective views, respectively, of a 4×6 cover plate array suspended over a 4×6 array of bicylindrical compartment vessels suspended over a 4×6 plate array of magnets, with one cylindrical magnetic stirrer showing, in accordance with one or more embodiments of the invention.
Figure 4B:
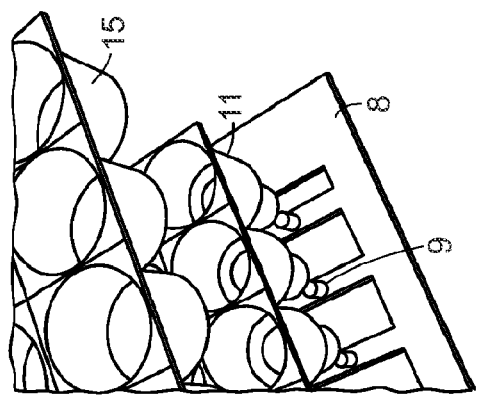
Figure 4A:
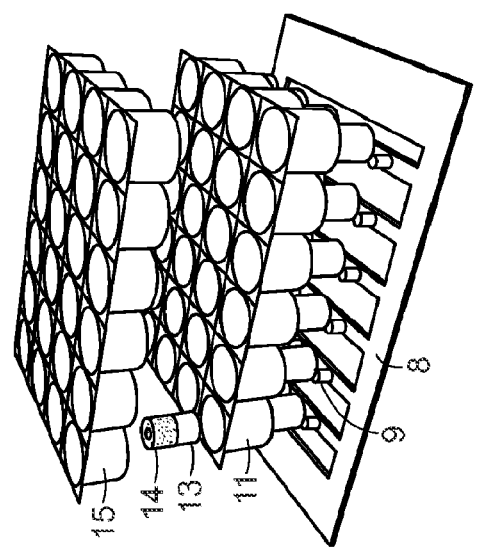
Figure 5B:
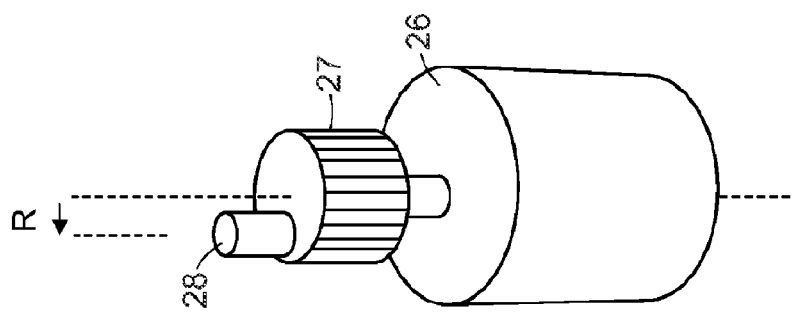
FIG. 5b is an enlarged perspective view of the motor drive for one of the pulleys having an off-axis pin to produce rotation motion of the array of magnets in accordance with one or more embodiments of the invention.
Figure 5A:
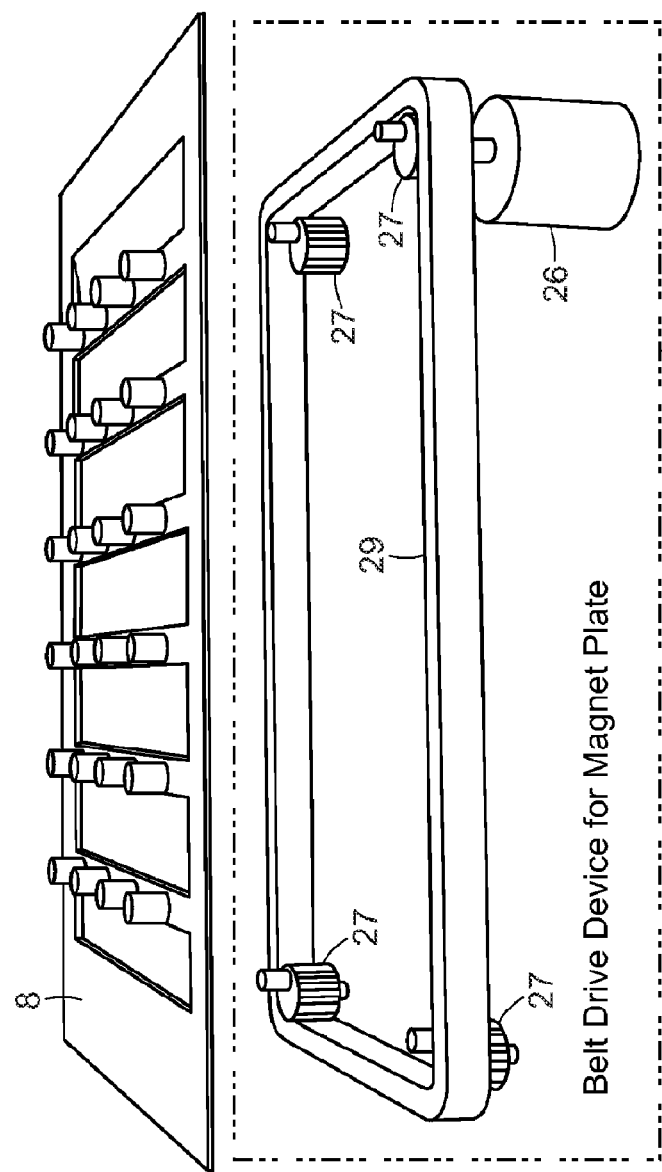
FIG. 5a is a perspective view illustrating a mixing device including a belt-driven pulley system detached from the underside of a 4×6 array of magnets in accordance with one or more embodiments of the invention.

FIGS. 5a and 5b illustrate a mixing device in accordance with one or more embodiments of the invention. The mixing device includes a belt-driven platform as shown in FIG. 5a comprising (in bottom-to-top order, respectively) a stationary (with respect to platform 3) sub-platform to which a belt and pulley drive 25 system is attached to four (or two-three as in some embodiments) bearing housings. The system rotates a plate of an array of magnetic drive elements 8 (FIGS. 2-5). A motor 26 (FIG. 5b) rotates a pulley 27, on top of which is a pin 28, displaced or offset from the axis of rotation of the motor by radius R. The radius R generally matches the radius of the vessels of the microtiter plate in which the dissolution process takes place. Four (or two as in some embodiments) pulleys 27 are linked by a geared belt 29, where the four pins 28 are inserted into four bearing housings located on the array of magnetic drive elements plate 8, such that the rotation caused by motor 26 effects the plate of magnetic drive elements 8 to rotate with a radius of rotation R (FIG. 5a). The pulley systems have the same rotational phase angle.

Figure 5C:
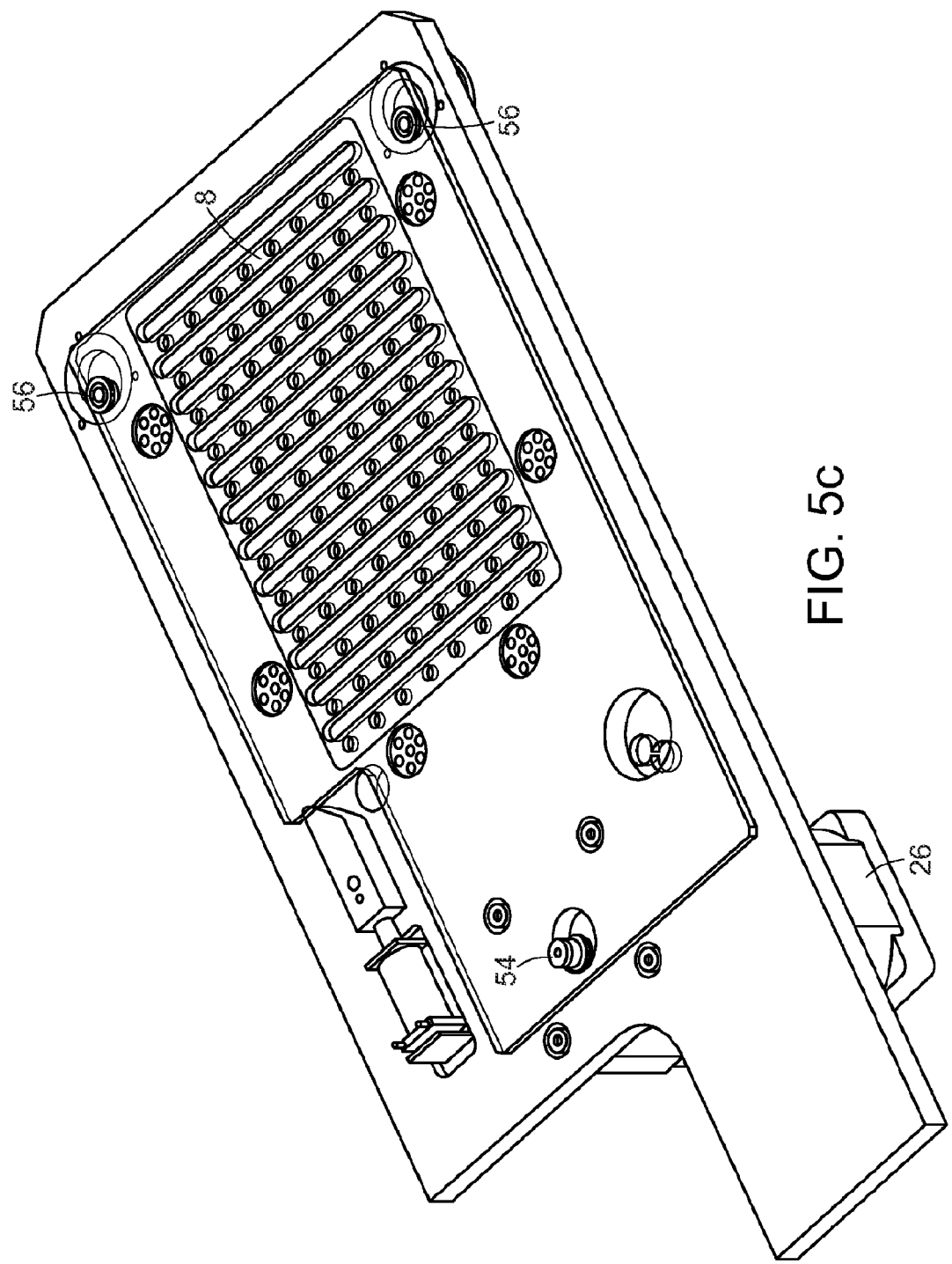
FIG. 5c is a perspective view illustrating an alternative mixing device without a pulley system in accordance with one or more embodiments of the invention.

An alternative mixing device in accordance with one or more embodiments, which does not include a belt drive mechanism, is shown in FIG. 5c. In this mixing device, the plate of magnetic drive elements 8 is driven by the motor 26 via a cam and follower mechanism, which causes each of the magnetic drive elements to move in a generally circular path having a radius that generally matches the radius of the vessels. A cam 54, which is turned by the motor 26, cooperates with a pair of followers 56 to cause the plate of drive elements 8 to move in the rotating pattern.

Figure 5D:
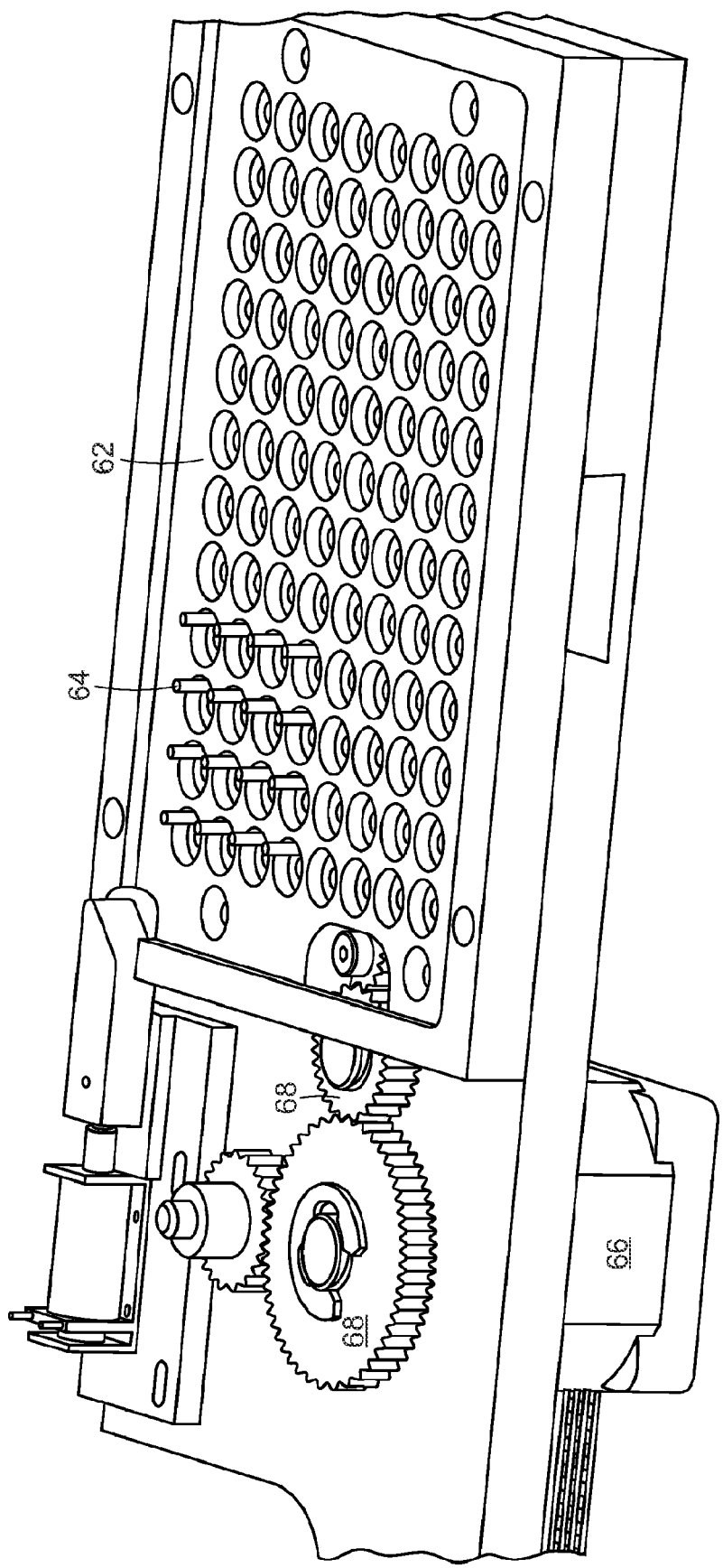
FIGS. 5d-f are perspective views illustrating another alternative mixing device having an array of inter-meshed gears in accordance with one or more embodiments of the invention.
Figure 5E:
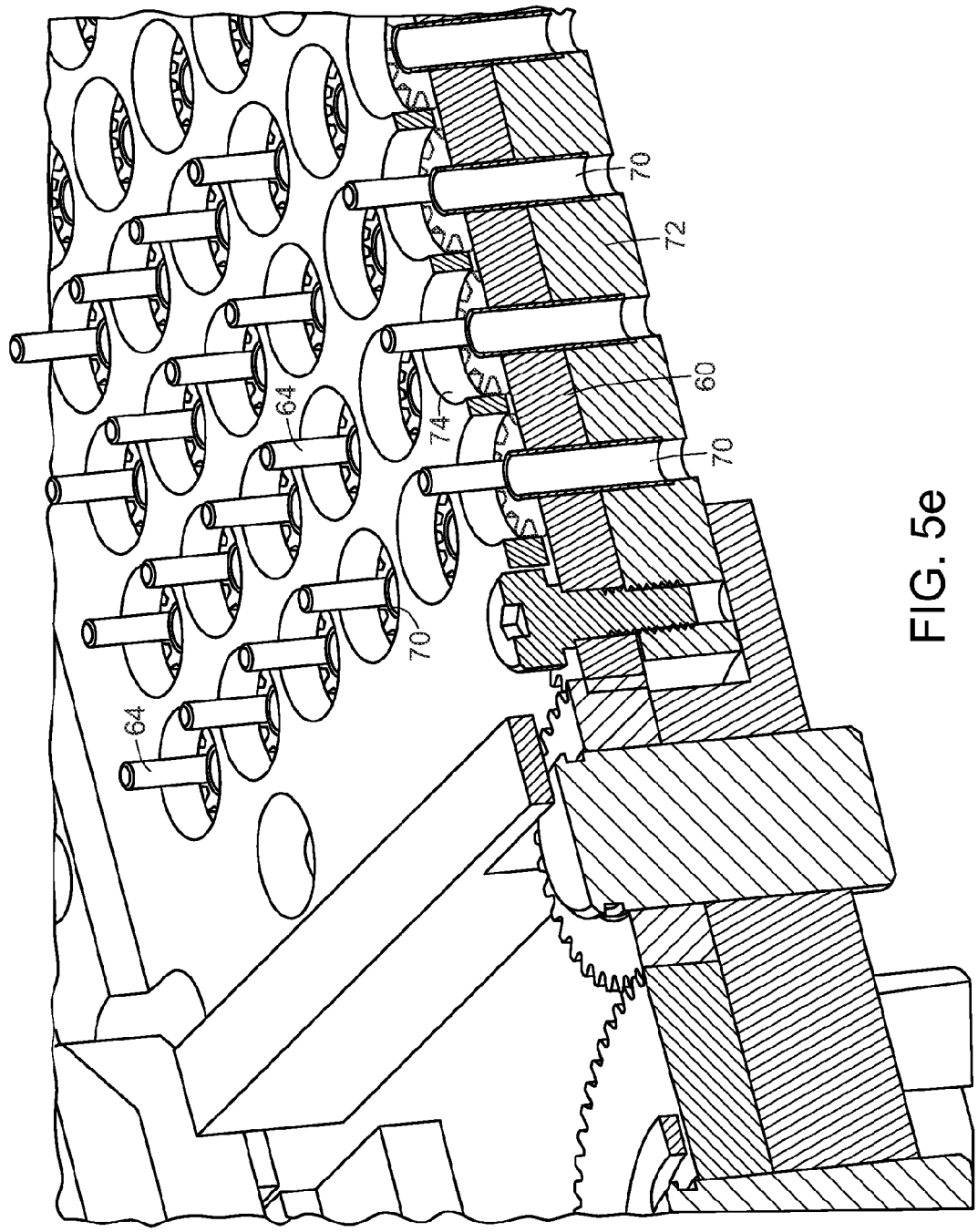
Figure 5F:
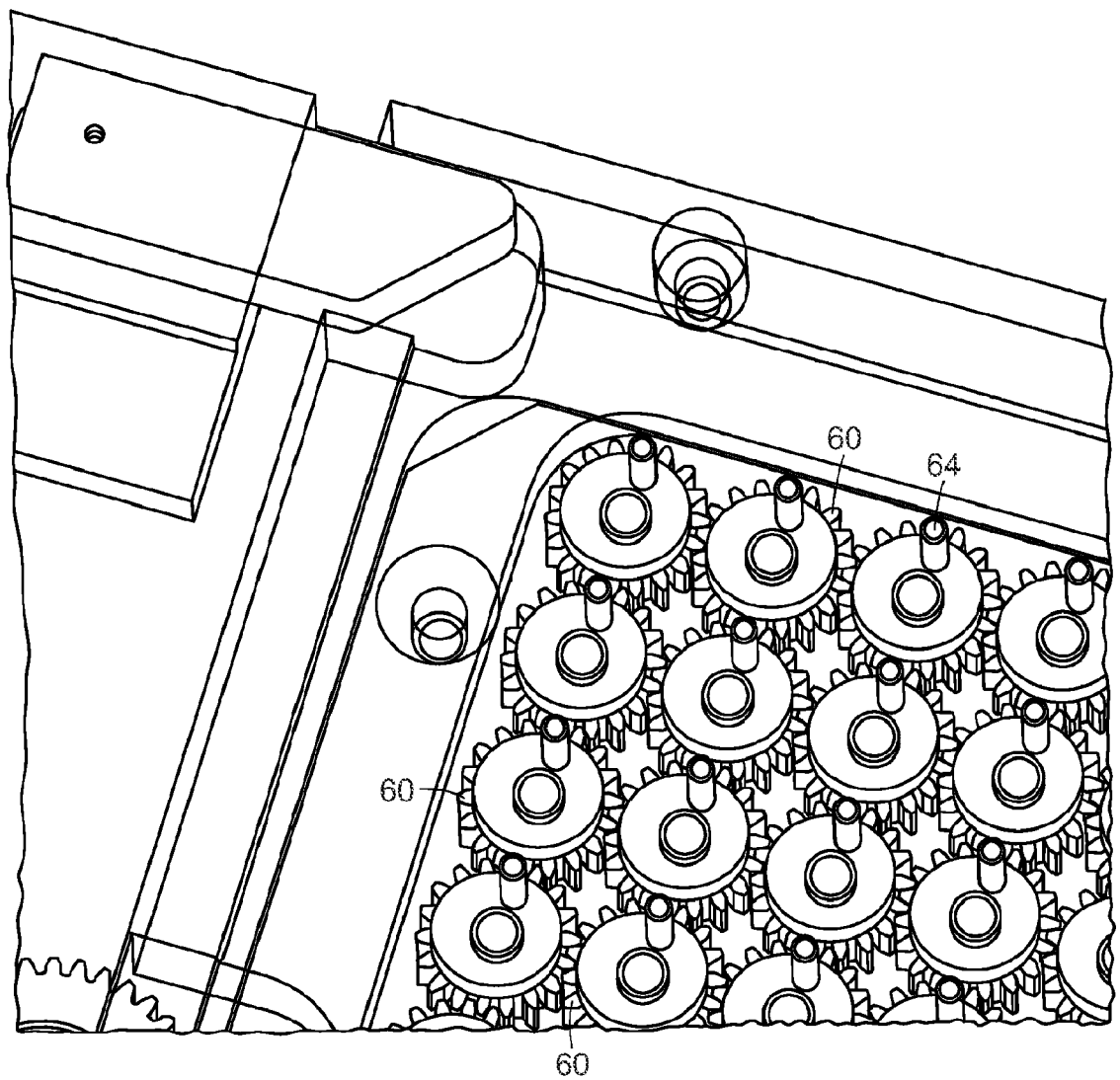

Another alternative mixing device in accordance with one or more embodiments is shown in FIGS. 5d-5f. FIG. 5d is a top perspective view of the mixing device. FIG. 5e is an enlarged perspective view of the mixing device with portions cutaway for purposes of illustration. FIG. 5f is a top perspective view illustrating the inter-meshed gears of the mixing device. The mixing device includes an array of inter-meshed gears 60 that are packaged in a cassette 62. Each of the gears 60 includes a magnetic drive element 64 positioned at an off-center location on said gear 60. The location of the magnetic drive element 64 on the gear 60 (i.e., the distance it is offset from the center of the gear 60) corresponds to the radius of the circular path the drive element will follow upon rotation of the gears 60. This radius will generally correspond to the radius of the vessels 7, 11 of the microtiter plate. (In FIGS. 5d and 5e, only selected magnetic drive elements 64 are shown for ease of illustration.)

Each of the gears 60 has teeth that are meshed with teeth of one or more adjacent gears 60 (FIG. 5f) such that the gears 60 all turn simultaneously. A motor 66 (FIG. 5d) engages the array of gears 60 via one or more spur gears 68 to simultaneously turn each of the gears 60 and drive elements 64 positioned thereon. In some embodiments, the motor 66 is a stepper motor.

As shown in FIGS. 5e and 5f, the center of each gear includes an open passage defined by a tube 70. The passage allows the light beam 20 to be transmitted such that it can pass through the mixing device and sample materials in the vessels.

As shown in FIG. 5e, in some embodiments, the gears 60 are sandwiched between a baseplate 72 and a retainer plate 74, thereby forming a stirring cassette. Each of the tubes 70 is press fitted into holes in the baseplate 72. The holes are drilled in the baseplate 72 and arranged in an array that matches the array of vessels 7, 11 of a microtiter plate. The center hole of each gear 60 is then slipped over a tube 70 such that the gears 60 are inter-meshed with adjacent gears 60. The array of gears so arranged matches the array of vessels 7, 11 in a microtiter plate. The gears 60 are held in place and do not spin off the tubes by being encapsulated between the baseplate 72 and the retainer plate 74. The retainer plate 74 is fastened to the base plate 72 to form the stirring cassette. The cassette is mounted to a shuttle plate of the platform 3 that will move the mixing device and microtiter plate into and around the inside of the analytical device 1.

Positioned above (but not touching) the rotating plate of magnets 8 is an optional stationary conductive block (e.g., nonmagnetic metal). The purpose of the conductive block (not shown in the figures) is to maintain the temperature of the solutions in the vessels placed in contact with it substantially constant, either at 25° C. or 37° C., or at similar temperatures. The temperature may be regulated by electrical heating, and/or by cooling/heating with a thermoelectric device (e.g., Peltier device). (Other thermostating means should be evident to those skilled in the art.) Above the thermal block and inserted into the thermal block is an array of vessels 7 as in FIG. 2 (or 11 as in FIG. 3). The array of vessels 7, 11 is in part or in whole made of material that allows for the substantial transmission therethrough of a beam of light 20. Placed into each individual vessel is a spherical magnetic stirrer 10 (or cylindrical magnetic stirrer assembly 12). In some applications, such as low pH, it is desirable to have the spherical magnetic stirrers 10 coated by an inert material, such as peralene or Teflon. In some embodiments, the magnetic stirrer element may be coated by a soft inert material or may be embedded in a buoyant inert material, so as to reduce the milling effect of the moving magnetic stirrer element. When working at higher temperatures, such as 37° C., it is desirable to cover the solution surface in each vessel of the array of vessels 7, 11. FIG. 4 shows such an optional cover plate 15. The cover plate comprises an array of descendent flat-bottom cups, which can be inserted into the vessels of 7, 11, displacing the air above the solutions, and resting on top of the solutions, said cover being not so heavy as to displace the liquid appreciably. In some embodiments, smaller sub-arrays of covers may be desirable, so that the whole array of vessels may have different sets of volumes of solution, constraining optical path lengths (inside the test liquid) for the beam of light 20 to a set of values. The cover plates are in part or in whole made of material that allows for the substantial transmission there-through of a beam of light 20.

The motion of the plate of magnets 8 vis-à-vis a stationary array of vessels 7, 11 is relative. For example, in some other embodiments (not necessarily preferred), the plate of magnets 8 may be stationary while the array of vessels 7, 11 moves in relation to it, as should be understood by those skilled in the art, given the description of the said preferred embodiment.

Figure 6C:
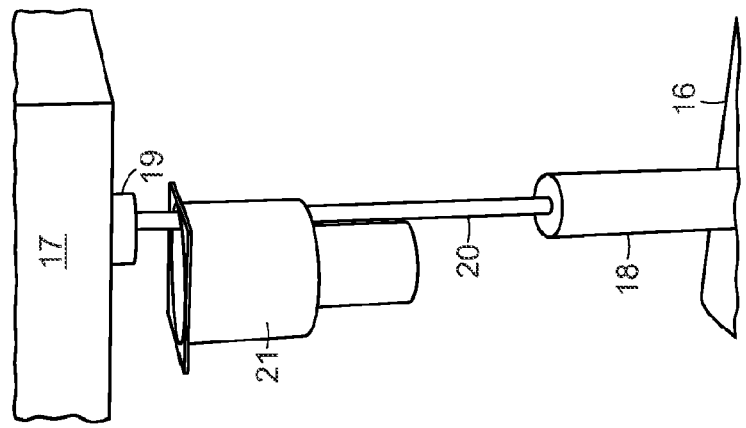
FIGS. 6a-6c are perspective views of the light source producing a collimated beam of light, which shines through the underside of the upper compartment of a single bicylindrical vessel and emerges above the vessel, and directed into a focusing lens unit of the analytical unit in the upper part of the figure, in accordance with one or more embodiments of the invention.
Figure 6B:
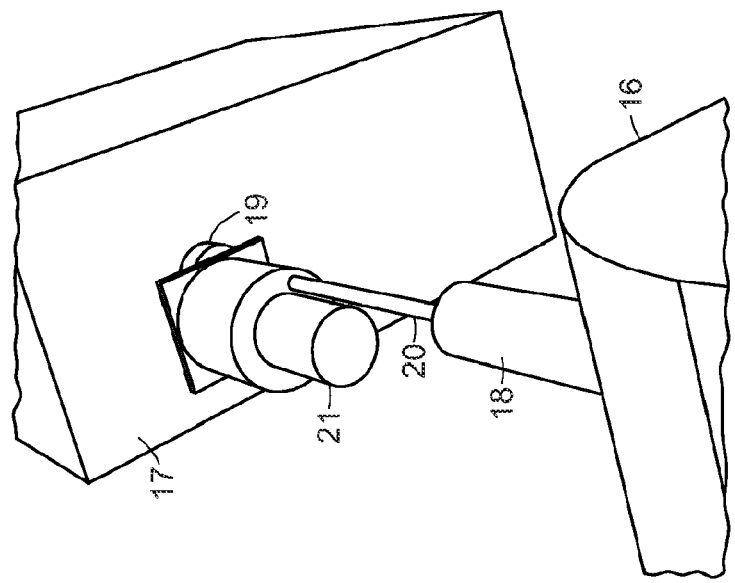
Figure 6A:
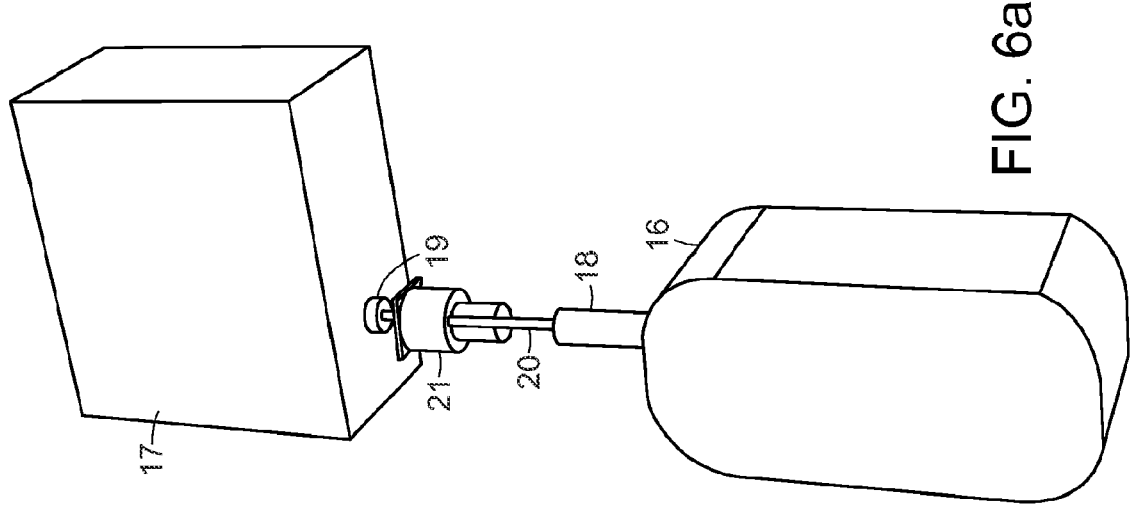

A light source 16 (UV/Vis, etc.) is located below platform 3, in a rigidly fixed position (with respect to the frame of analytical device 1). A collimator 18 guides a beam of light 20, preferably 1 mm in diameter, so that it passes through the vessel 21 (one of an array of bicylindrical vessels 11, each vessel with a cylindrical magnetic stirrer housing in the lower compartment), said vessel 21 holding the dissolution medium, as shown in FIG. 6. In the case of spherical magnetic stirrers 10 (cf., FIG. 2), the beam of light 20 shines through the center of the single-cylinder vessel in array 7, as the spherical magnetic stirrer 10 rolls along the perimeter of the vessel. As aforementioned, vessel 21 is made of material allowing for the substantial transmission of the beam of light 20, so that analytical absorption of light takes place principally in the dissolution medium, and not, e.g., in the walls of the vessel. The transmitted beam of light 20 is captured by a focusing lens 19, located on the surface of spectrophotometer 17, which in turn is located in a rigidly fixed position (with respect to the frame of said analytical device 1) above platform 3. Such sources of light 16 are available, e.g., from Heraeus Noblelight LLC (Duluth, Ga., USA). Such a spectrophotometer 17 is available, e.g., from tec5 USA (Plainview, N.Y., USA).

The plate of magnets 8 (FIGS. 2-5) contains slots between column arrays of magnets 9, such that during the rotation motion, at least some angles of rotation allow the beam of light 20 to pass through the vessel unobstructed (e.g., as in FIG. 4c). Alternately, the base plate is made of material allowing for the substantial transmission of the beam of light 20 there-through.

In accordance with one or more embodiments of the invention, the array of magnets preferably has at least two orientations allowing full transmission of the beam of light from light source 16 and at least two orientations fully blocking the transmission of the beam.

In accordance with one or more embodiments of the invention, the array of magnets oscillates in a plane coplanar (i.e., in parallel planes) to the array of vessels with amplitude of displacement matching the dimension of said vessel element.

Figure 7D:
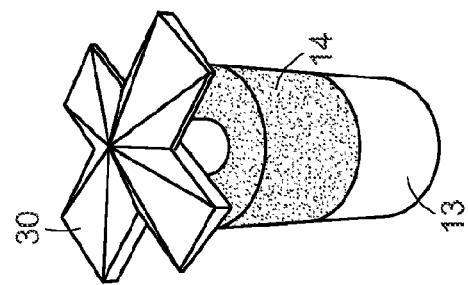
FIGS. 7a-7d illustrate four views of the cylindrical magnetic stirrer assembly, comprising a lower compartment containing a permanent magnet with north-south magnetic axis perpendicular to the cylindrical axis of the stirrer assembly, and an upper compartment metallic die containing a cylindrical hole used to contain sample compound compressed as a pellet (FIGS. 7a-c) or used to contain a stirrer blade insert when powder samples are used (FIG. 7d), in accordance with one or more embodiments of the invention.
Figure 7C:
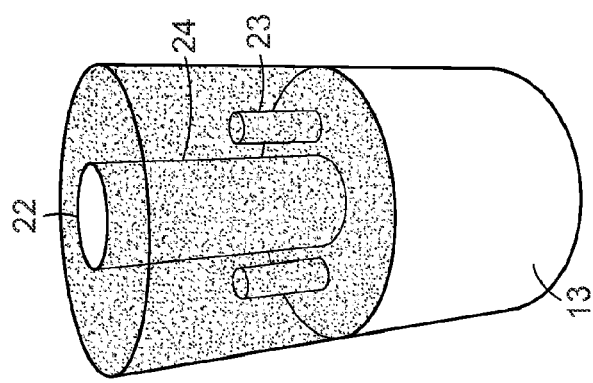
Figure 7B:
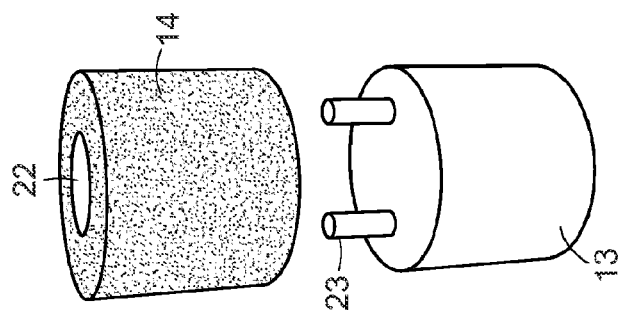
Figure 7A:
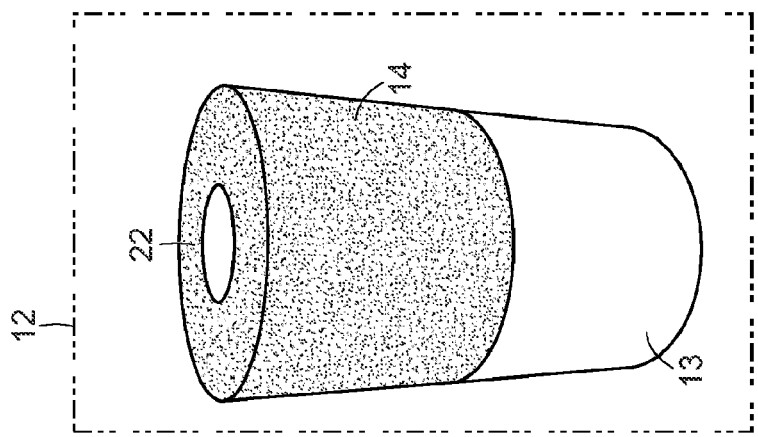

FIG. 7a shows in greater detail the cylindrical magnetic stirrer assembly 12 in accordance with one or more embodiments of the invention. The bottom component 13, preferably made of Teflon or hard polypropylene, has a permanent magnet embedded near its bottom (not shown in the drawings), with its north-south (N-S) axis preferably perpendicular to the cylindrical axis, so that the magnetic assembly 12 in the vessel 21 can be driven by the external rotating magnet 9 fixed on the rotating magnetic plate 8 in the position nearest the vessel containing the cylindrical magnetic stirrer assembly 12. Attached to the top of 13 is a hardened material die 14 (preferably of nonmagnetic stainless steel, or a hardened nickel alloy resistant to corrosion in acid solutions), with a cylindrical hole 24 in FIG. 7c (preferably with a 3 mm diameter) down its center, and two smaller holes in the bottom surface to receive two locating pins 23. The two main pieces of 12 are held in place by two locating pins 23 (FIG. 7b and FIG. 7c).

When the cylindrical magnetic stirrer assembly 12 is inserted into a bicylindrical vessel 21, the upper surface of the die 14 is essentially in the plane of the bottom surface of the upper cylindrical compartment of said vessel 21. Rotation of the cylindrical magnetic stirrer assembly 12 inside the lower cylindrical compartment of the bicylindrical vessel causes the fluid in the upper compartment of said vessel to symmetrically convect in a well-understood hydrodynamic manner (e.g., as summarized in Avdeef et al. "Dissolution and solubility." In: Comprehensive Medicinal Chemistry II, Vol. 5. Elsevier: Oxford, UK, 2007, pp. 399-423), causing the components of the fluid to uniformly mix in the cylindrical vessel.

When the sample compound is pressed into a pellet using the die 14 and an external pellet press, such as that available from Heath Scientific (Bletchley, Bucks, UK), the exposed surface of the compound 22 is flush with the upper surface of the die 14, with the compound pressed in cylindrical hole 24. As the compound at the surface of the rotating pellet dissolves during the dissolution period, the exposed surface area remains essentially constant. Such a feature is useful for intrinsic dissolution rate (IDR) measurements, as traditionally done with the so-called Wood's apparatus, often using 900 mL solution volumes and 500 mg sample weights. In accordance with one or more embodiments of the invention, such measurements can be performed in not greater than 3 mL volume, using not more than 5 mg of sample. In other optional embodiments, the volume and sample quantity can be further substantially reduced.

When the sample compound is a powder placed in the upper compartment of the bicylindrical vessel, the cylindrical magnetic stirrer device 12 can be modified by the insertion of a device such as a propeller-on-a-shaft 30 (preferably made of inert plastic) into the center hole 24 of the die 14. The entire assembly shown in FIG. 7d is inserted into a bicylindrical vessel 21 before the addition of powder sample into the upper cylindrical compartment of the bicylindrical vessel.

The simpler array of cylindrical vessels 7 (i.e., compared to the bicylindrical array of vessels 11) is designed to work with spherical magnetic stirrers 10 (cf., FIG. 2), and can be used predominantly with powder-sample compounds suspended in a liquid medium. This design can be readily applied to high-throughput screening. The simpler array of vessels design in FIG. 2 lends itself readily to larger density arrays of vessels, such as those containing 96 vessels in an 8×12 arrangement of vessels. Said embodiment of the invention allows such measurements to be done in preferably not greater than 0.2 mL volume, using preferably not more than a few micrograms of sample. Such high-throughput screening of compounds may be very useful in large drug discovery programs, where measurements are made over a short period of time and at ambient temperature, thus not requiring a cover plate and not requiring a thermal block to maintain constant temperature. This would lead to cost savings in the invention instrument embodiment.

The aforementioned fluidics-potentiometer device 2 can be used in place of an expensive robotic fluidic workstation. In that case, the combination of the analytical device 1 and the fluidics-potentiometer device 2 may comprise a cost effective system for performing a number of different micro assays, including those of dissolution, precipitation, solubility, stability, intestinal-model permeability, blood-brain barrier-model permeability, and the like, as should be evident to those skilled in the art of such high-throughput assays. Inside device 2 is a single (or a plurality of) pH-sensing electronic circuit board(s); in some configurations, eight-parallel pH sensing circuits are embedded. Also, inside device 2 are two to four high-precision dispensing syringe devices, preferably with 0.5 to 5.0 mL syringes, e.g., as those available from Cavro (Tecan Scientific Instruments, San Jose, Calif., USA). Devices partly like the fluidics-potentiometer device 2 are available, e.g., such as the pH QC Controller and also such as the Gemini Profiler instrument from pION INC (Woburn, Mass., USA).

In a preferred configuration of device 2 connected to device 1, a research-grade double junction combination semi-micro pH microelectrode 32 (FIG. 8a) is located inside device 1 (but in direct communication with the potentiometer part of device 2) held by a holder arm (not shown in the figures), which can lower the electrode into a dissolution vessel by the action of a solenoid-actuated drive, or the like. On an adjacent holder, two capillary tips for dispensing fluid can be lowered into or raised out of a dissolution vessel by the action of a second solenoid-actuated drive, or the like. In such a configuration, the fluidics-potentiometer device 2 has two dispensers and a single pH circuit to control the action of the pH measurement ensemble located inside device 1. Preferably, one of the dispensers is dedicated to dispensing Prisma™ universal buffer from an external container into each of the dissolution vessels inside device 1. The other dispenser is dedicated to dispensing standardized base titrant (preferably 0.5 M sodium hydroxide) from an external container, in very small (cf., FIG. 9, e.g., 21 nanoliter), but precise, volumes into the dissolution vessels, according to the user-specified pH, each vessel with its own specified pH. The specified pH is preferably in the range pH 1.2 to 8.0, more preferably in the range pH 5.0-7.4, and even more preferably at pH 6.8.

Preferred Embodiment for High-Throughput Permeability Monitoring

A permeability measurement system is mainly different from dissolution/solubility measurement system by the type of sample vessels used. The analytical device 1 and the fluidics-potentiometer device 2 are employed in a manner similar to that described above.

FIGS. 13-15 show two configurations of permeation cells that are elements of two arrays of vessels: donor and receiver.

Figure 13C:
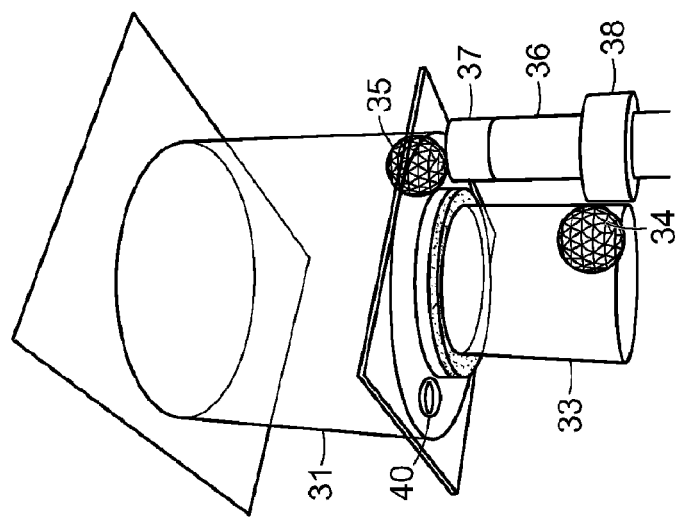
FIG. 13c illustrates a combined view, with two internal spherical magnetic stirrers and a rotating/oscillating external dual-magnet post, comprising an element of an array of dual-magnet stirrer posts mounted on a plate, in accordance with one or more embodiments of the invention.
Figure 13B:
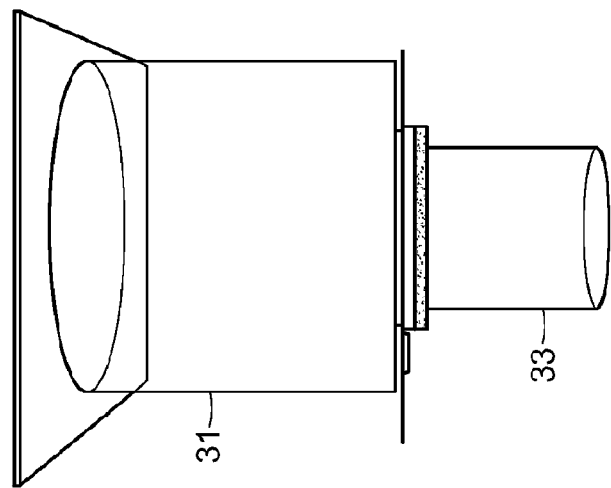
FIGS. 13a and 13b are separated and combined views, respectively, of a dual-compartment permeation cell of an array of such cells in accordance with one or more embodiments of the invention. The figures illustrate one donor vessel (bottom) of an array of vessels and one acceptor vessel (top) of an array of vessels, with acceptor vessel containing a membrane at its bottom, such that when the two vessels are combined, a dual-compartment permeation cell is formed.
Figure 13A:
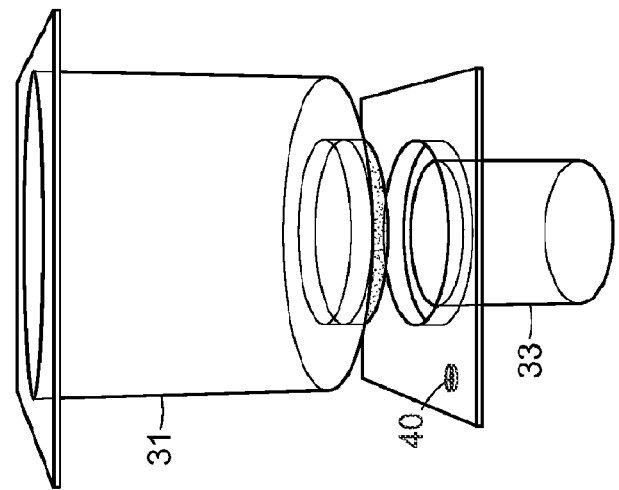
Figure 15D:
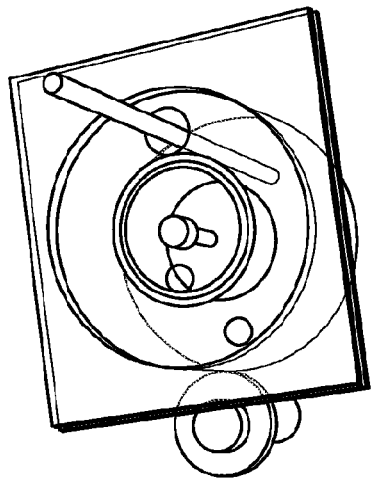
FIGS. 15a-15e are perspective and partially-exploded views of a dual-compartment permeation cell in accordance with one or more embodiments of the invention with a beam of light transmitting through the lower (usually receiver) vessel of a permeation cell comprising the upper vessel (usually donor) suspended inside the lower vessel (usually receiver), with the solution in the upper vessel separated from the solution in the lower vessel by a semi-porous membrane onto which a confluent layer of cells is placed, or a noncellular permeability barrier material is infused. The dual-vessel permeation cell shown is a member of an array of permeation cells.
Figure 15E:
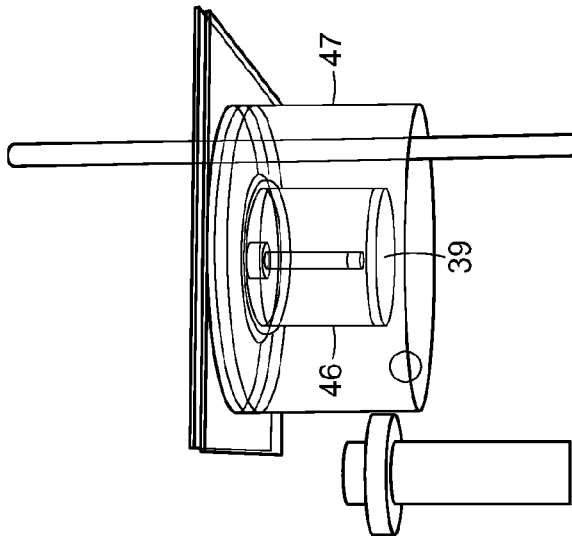
Figure 15B:
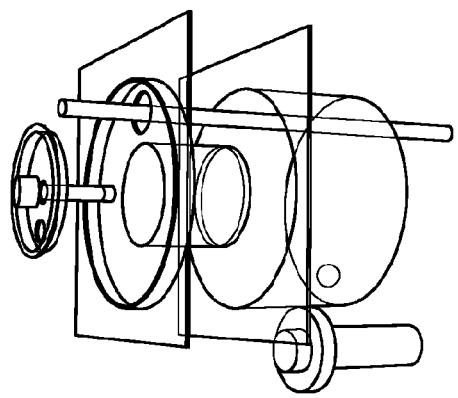
Figure 15C:
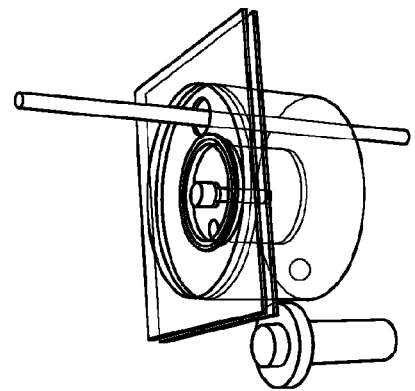
Figure 15A:
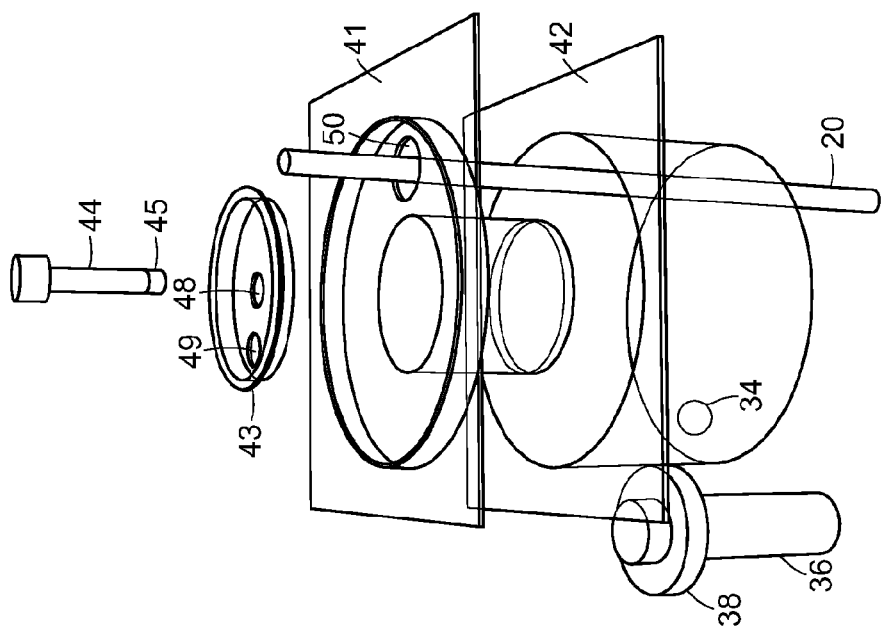

FIG. 13 shows the permeation cell assembly, exploded as in FIG. 13a, and combined as in FIG. 13b. The upper vessel 31 is the receiver compartment, and the lower vessel is the donor compartment 33. Two spherical magnetic stirrer elements, 34 and 35, are placed into each of the two compartments of the permeability cell, as shown in FIG. 13c. Pin 36 (made of nonmagnetizable material, such as a plastic rod or an aluminum tube) is an element embedded in the plate of magnets 8, which contains a toroidal magnet 38 (which magnetically couples to the donor spherical magnetic element 34) and a cylindrical magnet 37 (which magnetically couples to acceptor spherical magnetic element 35). The rotation of pin 36 around the perimeter of the donor vessel 33 causes the spherical magnets in the permeability cell to rotate, thereby effecting efficient stirring of the solutions in both compartments of the permeability cell.

FIG. 14 embodies the preferred configuration when the donor compartment 33 is below the receiver compartment 31. The objective is to monitor the concentration of the compound appearing (as a function of time) in the receiver compartment 31, said compound having been transported across the membrane barrier 39. The beam of light 20 emerging from the collimator 18 passes through an opening 40 in the donor vessel 33 into the bottom face of receiver vessel 31, said receiver vessel being made of material that does not appreciably absorb the beam of light. The beam of light 20 passes through the solution inside receiver vessel 31, wherein the chemical compound may absorb a portion of the beam of light as it passes through the solution. The transmitted beam of light then enters the focusing lens 19 of the spectrophotometric detector device 17.

FIG. 15 embodies the preferred configuration when the receiver compartment 47 is below the donor compartment 46. The objective is to monitor the concentration of the compound appearing (as a function of time) in the receiver compartment 47, said compound having been transported across the membrane barrier 39. The beam of light 20 passes through the bottom surface of the receiver vessel 42, said receiver vessel being made of material that does not appreciably absorb the beam of light. The beam of light 20 then passes through the solution inside receiver compartment 47, wherein the chemical compound may absorb a portion of the beam of light as it passes through the solution. The transmitted beam of light then passes through an opening 50 in the face 41 of the upper donor compartment 46, and enters the focusing lens 19 of the spectrophotometric detector device 17.

A spherical magnetic stirrer element 34 is placed into the lower receiver compartments 47 of the permeability cell, as shown in FIG. 15. Suspended in the cap 43 for the donor compartment 46 is a dongle 44 (made of nonmagnetizable material, such as a plastic rod or an aluminum tube with a flange on the top), containing a cylindrical magnetic element 45 attached to its bottom. The magnetic element 45 is suspended sufficiently above the surface of the membrane barrier 39 in all configurations so as not to disturb cellular layers attached to the membrane barrier 39. Pin 36 (made of non-magnetizable material, such as a plastic rod or an aluminum tube) is an element embedded in the plate of magnets 8, attached to which is a toroidal magnet 38, which magnetically couples to the receiver spherical magnetic element 34 and to the donor cylindrical magnetic element 45. The rotation of pin 36 around the perimeter of the donor compartment 47 causes the spherical and the dongle-suspended magnets in the permeability cell to rotate, thereby effecting efficient stirring of the solutions in both compartments of the permeability cell.

Opening 49 allows for the addition or sampling of fluid in the upper donor vessel.

Example 1

Dissolution Profiles for a Series of Model Drugs Collected with a Prototype Instrument, the μDISS Scanner™

Figure 10:
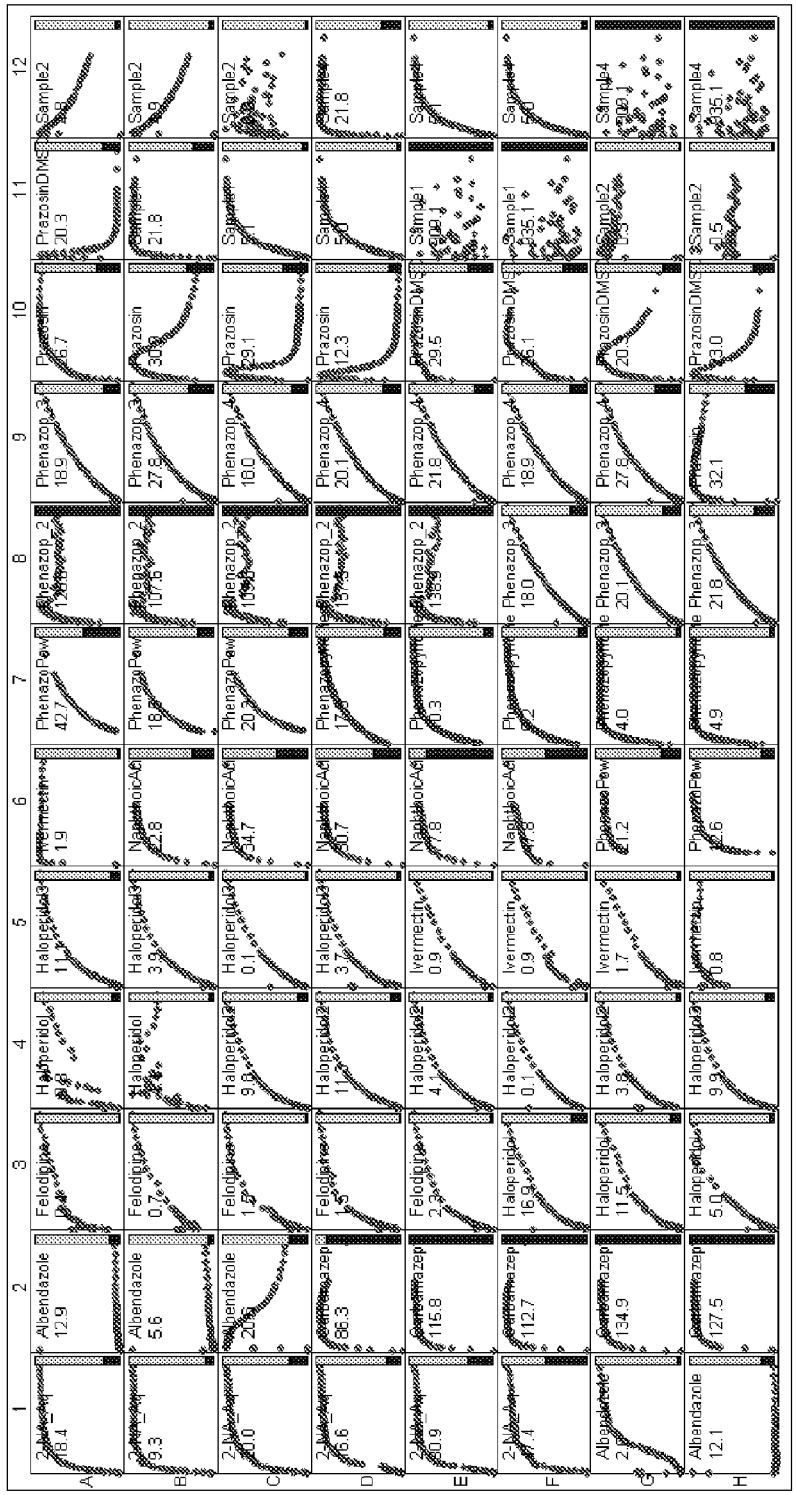
FIG. 10 is an exemplary screenshot illustrating a Client Report showing 96 dissolution curves in accordance with one or more embodiments of the invention.

FIG. 10 shows a μDISS Scanner™ Client Report for powder sample compounds, where each frame of 96-frame map depicts a dissolution profile (autoscaled), and contains the name of the model drug, the concentration dissolved as a numerical quantity, and a graphic bar (on the right side of the frame), which in two colors, represents the extent of the dissolution processes in each vessel, with the dark color representing the fraction dissolved and the light color representing the fraction undissolved. For example, cells G7 and H7 indicate that only a small proportion of the powder has dissolved. Some compounds, like prasozin in column 10, indicate rapid dissolution, followed by reprecipitation, which is consistent with polymorphic transformation, from active to inactive form. Similar patterns are sometimes observed when salts of compounds dissolve quickly initially, followed by patterns of reprecipitation of the free acid/base.

Example 2

Method for the Prediction of Dissolution Profiles Ahead of the Data Collection Time—Exponential Function The dissolution concentration-time profile may be described by an exponential equation, which is a solution to the Noyes-Whitney differential equation describing a simple dissolution process.

$$C(t) = S \cdot \left(1 - e^{-\frac{A}{V} \cdot P_{ABL} \cdot 60 \cdot (t-t_o)}\right) \quad [1]$$

where C(t) is the concentration of the API in solution at time t. The concentration is in units of μg/mL and time in minutes. As the dissolution data are being acquired, eq. 1 is applied to calculate the best-fit curve, based on the three parameters determined by weighted nonlinear least-squares refinement: (a) S, the solubility of the compound in the medium (pH 6.8), (b) A, the effective (or nominal) surface area of the compound (e.g., pressed pellet) exposed to the medium, and (c) $t_o$, the "lag" time, the offset time when the function crosses the zero at a non-zero time point. The other terms in eq. 1 are V, the medium volume in units of cm$^3$ (=mL), and $P_{ABL}$, the aqueous boundary layer (ABL) permeability, in cm/s units (converted to cm/min by the factor 60 in the equation). Both of these two terms are treated as constant known parameters. $P_{ABL}$ can be calculated from the ABL thickness (using the Levich equation) and the aqueous diffusivity of the sample compound, as described by Avdeef et al. "PAMPA—a Drug Absorption in vitro Model. 11. Matching the in vivo Unstirred Water Layer Thickness by Individual-Well Stirring in Microtitre Plates." Eur. J. Pharm. Sci., 2004, 22, 365-374. There are available computer programs, such as pCEL-X (pION INC, Woburn, Mass., USA), which can be used to calculate $P_{ABL}$ values.

Figure 11A:
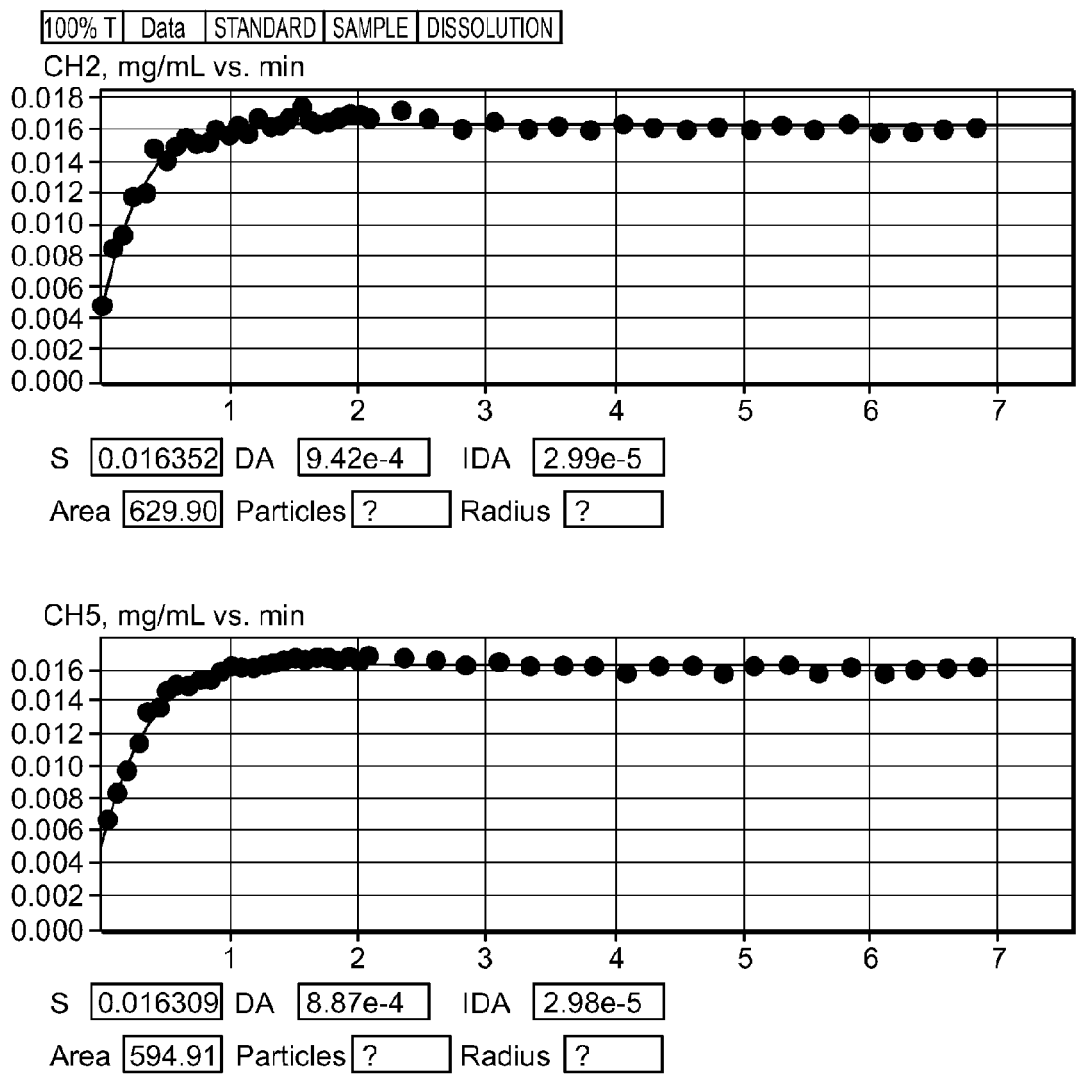
FIG. 11a is an exemplary screenshot illustrating dissolution data analysis, which predicts the outcome of the dissolution assay, in accordance with one or more embodiments of the invention.
Figure 11B:
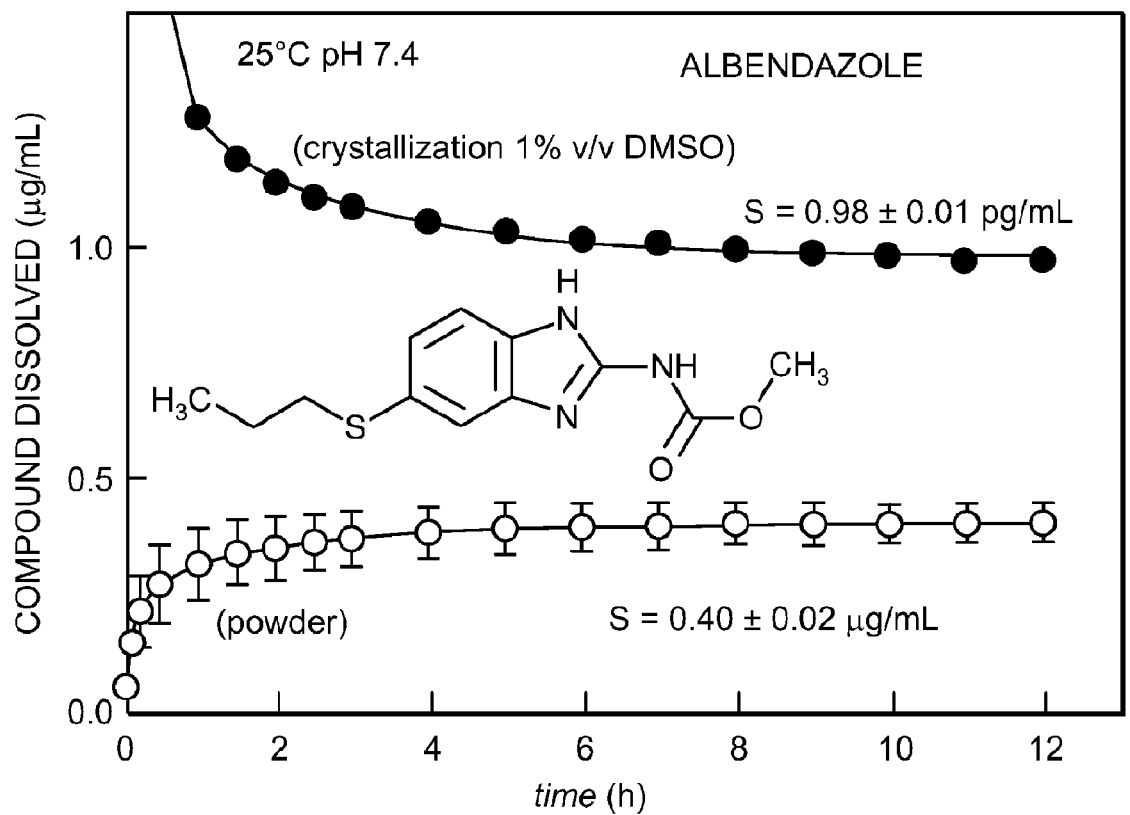
FIG. 11b is an exemplary plot illustrating precipitation of albendazole in a buffer solution containing 1% v/v dimethylsulfoxide (upper curve) and dissolution of a solid powder into the same buffer (lower curve).

FIG. 11 shows the individual readings of in situ determined concentration of two dissolution profiles, where the sample was a very small tablet containing fast release of nitroglycerin, an angina medicine. Half of the API in the mini tablets was released in about 6 seconds. This illustrates the in situ determination of concentration is fast, and cannot be easily mimicked by batch sampling, followed by HPLC concentration determination, as is the common practice in slower traditional methods.

The solid lines best-fitting the points are the result of real time processing of the data according to an exponential fitting of the data as the data are collected (eq. 1). The advantage of such in situ real time fitting is that the completion of the dissolution process can be predicted long before the equilibration is actually achieved.

Example 3

Method for the Prediction of Dissolution Profiles Ahead of the Data Collection Time—Biexponential Function This example is based on the dissolution and solubility characteristics of the model drug carbamazepine, with data collected on a prototype instrument, utilizing a miniaturized rotating disk of pressed compound held as a pellet in a small stainless steel die. The average diameter of the pellets of material was measured to be 3.9 mm, corresponding to a nominal area of 0.12 cm$^2$, and the minimal amount of compound needed to make such pellets was about 5 mg, although more may be used. In this example, the solution volume was 15 mL, larger than the preferred volume of 3 mL. Over 1100 concentration measurements were acquired, in five replicate dissolution profiles.

It was observed that a single exponential function, such as eq. 1, does not fit the data very well. A physical reason for this may be that the miniature pellet may have had some small amount of loosely packed powder on the surface of the pellet and from other irregularities of the press operation. It had been noted that the initial dissolution process indicated a "burst" of quickly dissolving material, followed by a much slower process of pellet dissolution. A model that may explain this behavior is proposed below. Consider that there are two surface areas in the entire dissolution process. The powder "burst" would be associated with a high surface area, but would be limited to a small quantity of material:

$$C(t) = C_{powder} \cdot \left(1 - e^{-\frac{A_{powder}}{V} \cdot P_{ABL} \cdot 60 \cdot (t-t_o)}\right) + \\ C_{pellet} \cdot \left(1 - e^{-\frac{A_{pellet}}{V} \cdot P_{ABL} \cdot 60 \cdot (t-t_o)}\right) \quad [2]$$

Figure 12:
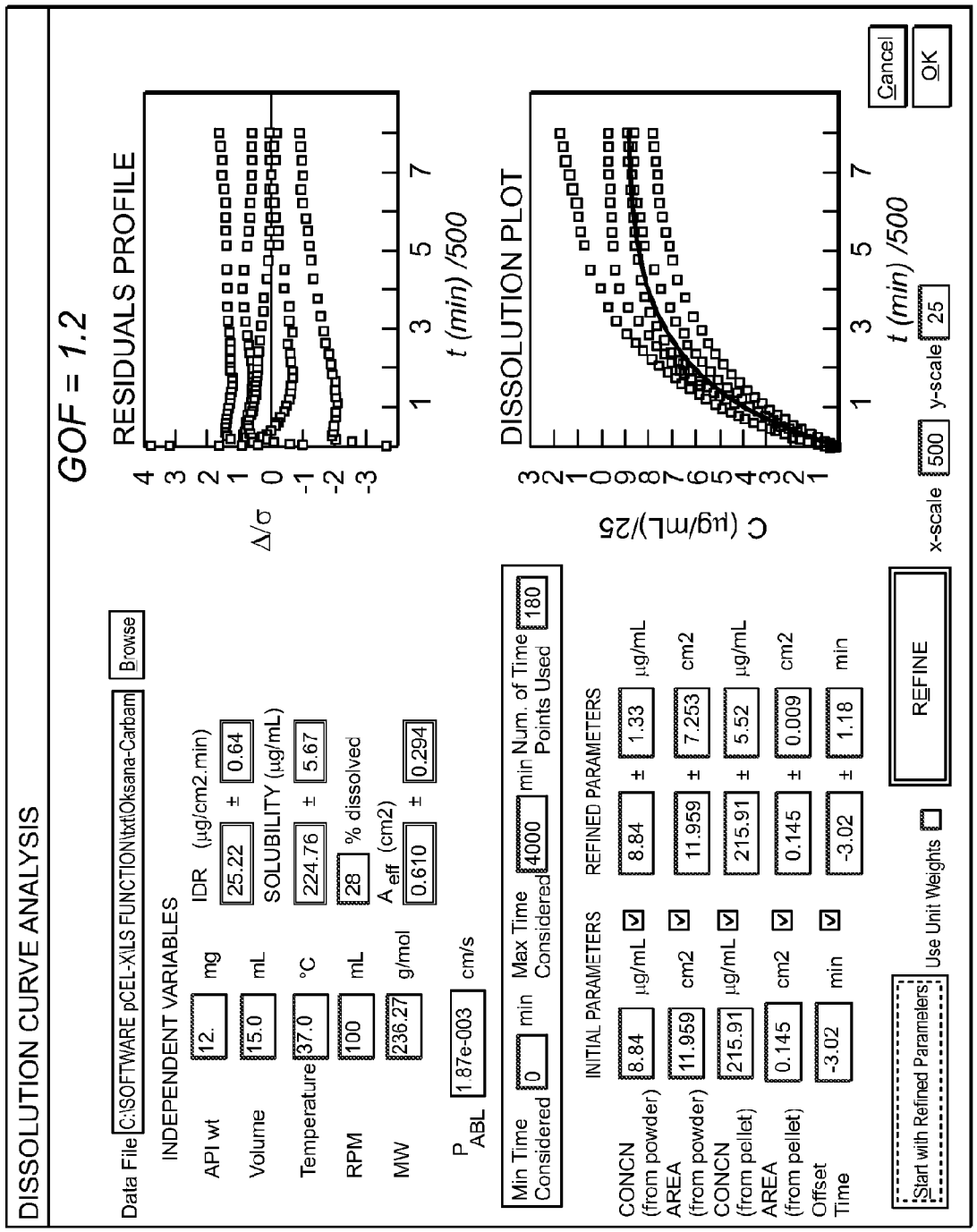
FIG. 12 is an exemplary screenshot illustrating the analysis of five dissolution curves using a biexponential function in accordance with one or more embodiments of the invention.

In this definition, $C_{powder}$ refers to the concentration in the final saturated solution due to the contribution of the powder "burst." The area associated with the powder is $A_{powder}$. The second term contains the contribution from the pellet, such that at very long time, the sum of the two concentration terms would be equal to the solubility, provided that the solution is saturated at equilibrium at the end of the assay. FIG. 12 summarizes the results of the analysis, with IDR=25±1

µg/cm²·min and S=225±6 µg/mL, based on selected 180 evenly-spaced points out of the total of about 1100 measurements.

The dissolution rate (DR) is defined as the change of dissolved mass per change in time. The biexponential dissolution equation (eq. 2), when multiplied by the volume, describes mass dissolved as a function of time. The first derivative of the function is maximum at the start of dissolution, and becomes zero at infinite time, when either all the solid has dissolved or when the solution becomes saturated, with the presence of undissolved excess solid. It is most useful to derive the maximum dissolution rate, $DR^{max}$, to characterize the speed of dissolution. The first derivative of eq. 2 with respect to time, evaluated at $t=t_o$, in the units of µg/min (with $P_{ABL}$ in cm/s units), is $$DR^{max}=(C_{powder}\cdot A_{powder}+C_{pellet}\cdot A_{pellet})\cdot P_{ABL}\cdot 60 \qquad [3]$$

The factor of 60 accounts for the conversion of ABL permeability into cm/min units. Intrinsic dissolution rate (IDR) is calculated as $IDR=DR^{max}/A_{eff}$, where $A_{eff}$ is the effective area of the solid phase in contact with bulk solution. The effective surface area is defined as $A_{eff}=\delta A_{powder}+(1-\delta)A_{pellet}$, where $\delta=C_{powder}/(C_{powder}+C_{pellet})$. The IDR is the maximum flux of material entering the solution phase through the interface solid-liquid interface (often evaluated at time near zero). According to thin layer theory, the rate-limiting barrier is the thin water layer, most commonly known as the aqueous boundary layer (ABL), across which dissolving material diffuses into the bulk solution. Flux may be stated as a product function of solubility and permeability across the ABL: $IDR=flux=S\cdot P_{ABL}\cdot 60$. So, for the rotating disk method, there are two operationally different ways to estimate the IDR value in a dissolution experiment, depending on whether the solid completely dissolved at infinite time or whether a saturated solution forms then:

CASE 1 (fully dissolved at $t=\infty$, i.e., infinite time):
$$IDR=DR^{max}/A_{eff} \qquad [4a]$$

CASE 2 (saturated solution at $t=\infty$, i.e., infinite time):
$$IDR=C(t_\infty)\cdot P_{ABL} \qquad [4b]$$

In CASE 1, $DR^{max}$ is the based on the initial slope of the dissolution curve, and $A_{eff}$ is the calculated effective or the directly measured area of the rotating disk. In CASE 2, the concentration at $t=\infty$ (i.e., infinite time, as approximated by a long period of time) is just the solubility, and $P_{ABL}$ may be calculated by the aforementioned standard methods.

Example 4

Figure 9:
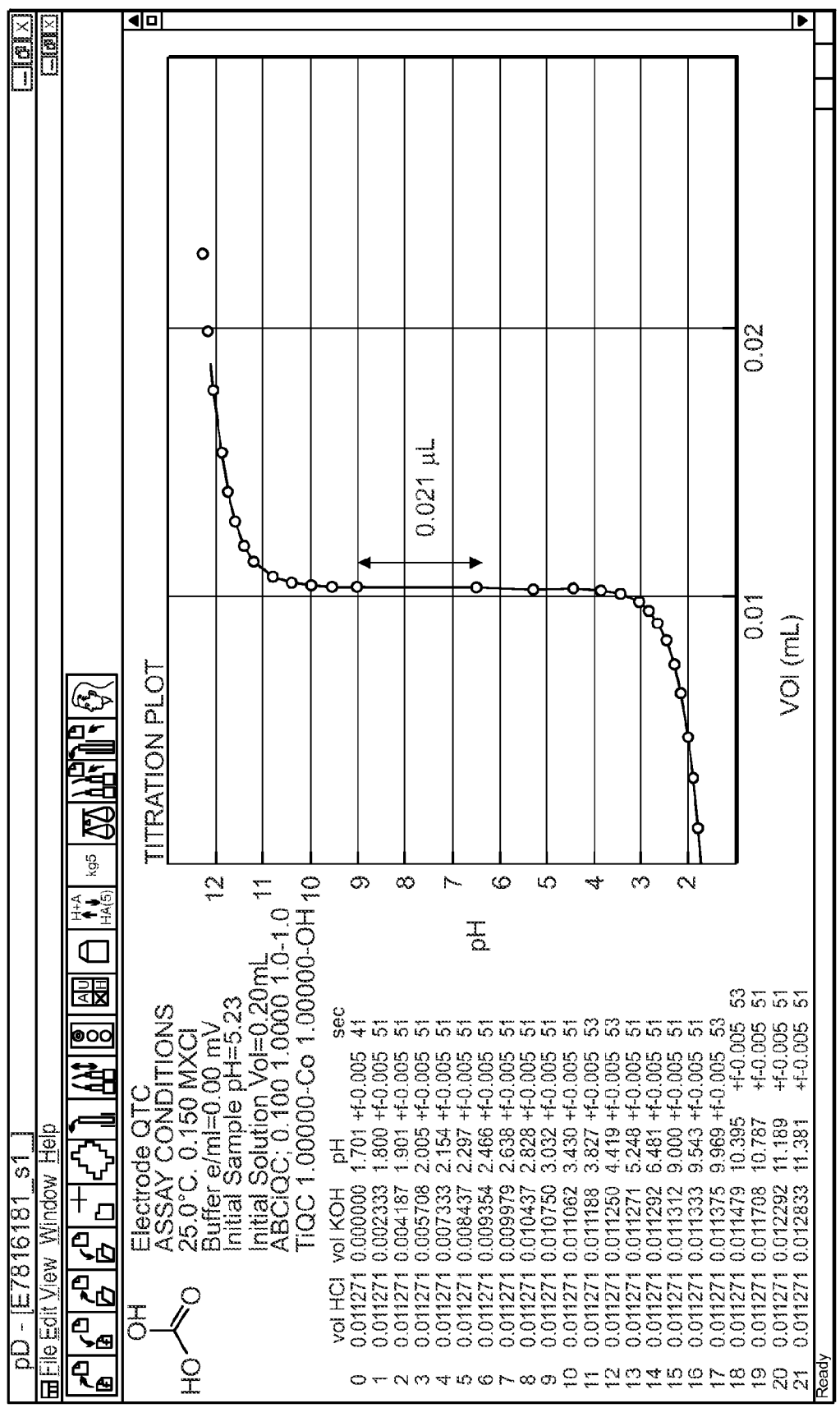
FIG. 9 is an exemplary screenshot illustrating a titration curve based on an alkalimetric pH titration in a solution volume of 0.14 mL in accordance with one or more embodiments of the invention.

Titration of a 140 Microliter Sample Solution in 96-Well Microtiter Plate Using a Ross® Micro pH Electrode FIG. 9 shows a titration curve, with pH as the dependent variable and volume (mL) of 0.5 M mineral base titrant added as the independent variable. In the neutral pH 7 region, the minimum added volume of titrant was 21 nanoliters, which produced a change of about 2 pH units in the steep part of the titration curve. Smaller changes in pH are evident in the buffered regions of the titration. This example illustrates that precise pH can be successfully measured in a microtiter plate vessel containing as little as 0.14 mL solution medium, while very small volumes of titrant additions are made to effect the pH to change controllably and reproducibly. In one embodiment of the invention, one vessel in an array of vessels will be reserved to carry out such an alkalimetric pH titration of a known volume of the Prisma™ universal buffer solution (e.g., as revealed by Avdeef and Tsinman in U.S. Pat. No. 6,569,686 B2) so as to establish a standard curve relating pH value to the titrant added. Such a calibration curve could be applied to adjusting pH to certain, user specified, values in each of 96-vessel microtiter plate vessels, without having to directly read the pH, thus speeding up the process of automatically preparing buffers in each vessel of a microtiter plate of vessels.

Figure 8C:
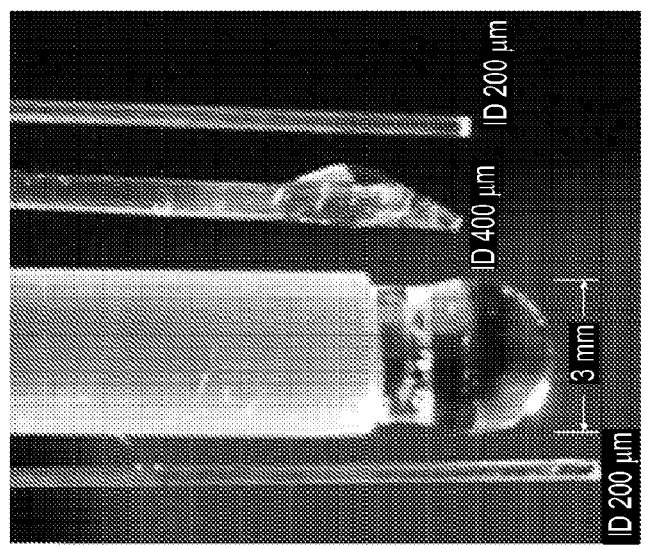
FIG. 8(c) is a close-up view of the micro electrode, along with quartz-capillary solution delivery tips in accordance with one or more embodiments of the invention.
Figure 8B:
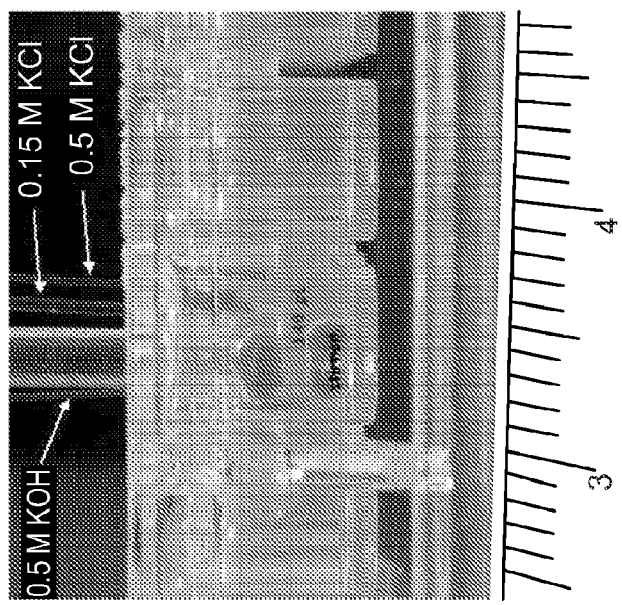
FIG. 8(b) is a perspective view for a micro pH electrode (Thermo Ross® brand) in one vessel of a 96-well microtiter plate in accordance with one or more embodiments of the invention.
Figure 8A:
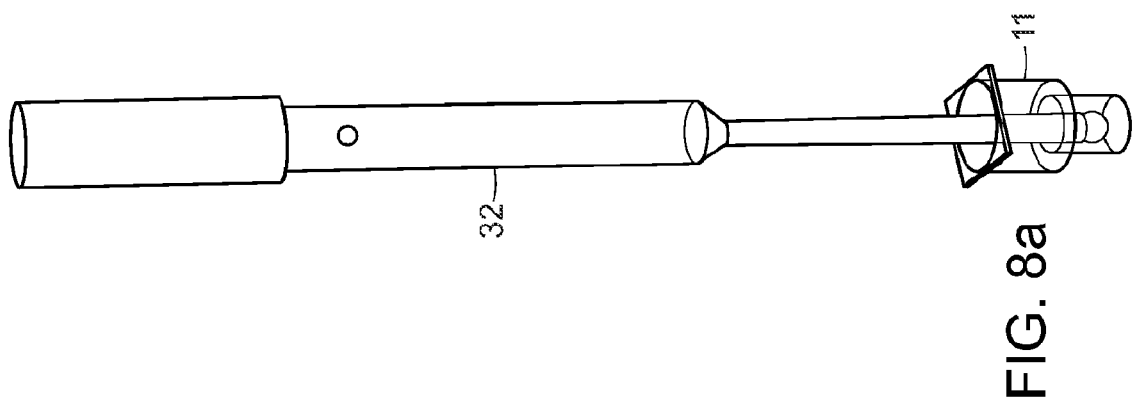
FIG. 8(a) is a perspective view of a semi-micro pH electrode inserted into the lower compartment of a bicylindrical vessel in accordance with one or more embodiments of the invention.

FIG. 8b shows the titration taking place in one vessel of a 96-well microtiter plate. FIG. 8c shows the electrode and three dispenser fluid delivery capillaries close-up. The pH sensing bulb of the electrode has a radius of 1.5 mm, and the titrant delivery capillaries have inner diameters of 0.2 mm, while the delivery capillary reserved for the Prisma™ universal buffer has a diameter of 0.4 mm.

Having described preferred embodiments of the present invention, it should be apparent that modifications can be made without departing from the spirit and scope of the invention.

The invention claimed is:

1. A mixing system for use in an apparatus for evaluating physicochemical properties of sample materials contained in an array of vessels, the apparatus including a light detector, a light source for transmitting a light beam through the sample material in a vessel to the light detector, and an analyzer for processing data from the light detector to determine concentration-related properties of the sample material as a function of time, the mixing system comprising:
    a plurality of magnetic stirrer elements, each for being placed in a sample material in a different one of the array of vessels;
    an array of magnetic drive elements, each associated with a different one of the array of vessels and being magnetically coupled with a magnetic stirrer element in an associated vessel; and
    a drive mechanism coupled to the array of magnetic drive elements for simultaneously moving each of the magnetic drive elements relative to an associated vessel to cause corresponding movement of the magnetic stirrer element in the associated vessel to stir the sample material;
    wherein the array of magnetic drive elements and the drive mechanism are configured to enable passage of the light beam from the light source through the sample material in each vessel to the light detector such that a concentration-related property of the sample material contained in a vessel can be detected as a function of time while the sample material is being stirred by a magnetic stirrer element.

2. The mixing system of claim 1 wherein the array of vessels remains generally stationary while the sample materials are stirred by the stirrer elements.

3. The mixing system of claim 1 wherein drive mechanism moves each of the magnetic drive elements in a generally circular path relative to and in close proximity to an associated vessel to cause corresponding movement of the magnetic stirrer element in the associated vessel in a generally circular path about the periphery of the associated vessel to stir the sample material therein.

4. The mixing system of claim 1 wherein magnetic stirrer elements are spherical or cylindrical in shape.

5. The mixing system of claim 1 wherein either each of the magnetic stirrer elements comprises a permanent magnet, or each of the magnetic drive elements comprises a permanent magnet, or both each of the magnetic stirrer elements and each of the magnetic drive elements comprises a permanent magnet.

6. The mixing system of claim 1 wherein the light beam passes through the sample material in a vessel in a generally vertical direction.

7. The mixing system of claim 1 wherein the drive mechanism comprises an array of gears corresponding to the array of magnetic drive elements, each of said gears having teeth that are meshed with teeth of one or more adjacent gears and having a corresponding magnetic drive element positioned at an off-center location on said gear, said drive mechanism further comprising a motor for simultaneously turning each of the gears and drive elements positioned thereon.

8. The mixing system of claim 7 wherein each of said gears includes an opening at the center thereof through which said light beam can be transmitted such that it can pass through the sample material in an associated vessel.

9. The mixing system of claim 1 wherein the drive mechanism comprises a platform on which said array of magnetic drive elements is positioned, and said drive mechanism further comprises a motor engaged with the platform to move the platform in a manner that causes each of the magnetic drive elements to move in a generally circular path having a radius generally corresponding to the inner radius of one of said vessels.

10. The mixing system of claim 9 wherein said platform includes one or more openings to allow said light beam to pass therethrough from the light source through the sample material in each vessel to the light detector.

11. The mixing system of claim 1 wherein said concentration-related properties comprise ultraviolet/visible/near-infrared absorption or transmittance, fluorescence, or luminescence.

12. The mixing system of claim 1 wherein the concentration-related property detected as a function of time can be analyzed to obtain physicochemical properties including dissolution characteristics, equilibrium solubility characteristics, kinetic solubility characteristics, precipitation characteristics, or membrane permeability characteristics of the sample materials.

13. The mixing system of claim 1 wherein the array of vessels comprise wells of a microtitre plate, said microtitre plate comprising a material that allows appreciable transmission therethrough of said light beam.

14. The mixing system of claim 1 wherein the sample material in each of the vessels has a volume of less than about 3 mL.

15. The mixing system of claim 1 wherein the data are repetitively acquired for each time point in less than three seconds per sample material in a vessel.

16. The mixing system according to claim 1 further comprising a temperature control mechanism for maintaining said sample materials at a generally predetermined temperature.

17. The mixing system according to claim 1, further comprising a cover plate for covering each of said vessels to inhibit evaporation of the sample material therein, said cover plate including an array of projections, each projection fitting in a different one of said vessels to displace air in the vessel above the sample material.

18. The mixing system according to claim 1 wherein said light beam is a collimated light beam produced by a lamp selected from a group consisting of: (a) an ultraviolet-spectrum emitting lamp, (b) a visible-spectrum emitting lamp, (c) a combination ultraviolet-visible lamp, (d) an infrared-spectrum emitting lamp, and (e) a near-infrared-spectrum emitting lamp, and wherein said light detector is a detector selected from the group consisting of: (a) an ultraviolet-visible detector, (b) an infrared detector, (c) a near-infrared detector, (d) a fluorescence detector, and (e) a luminescence detector.

19. The mixing system according to claim 18 wherein said light detector is a photodiode array of elements (PDA) or a charge-coupled device (CCD) or a photomultiplier device (PM).

20. The mixing system according to claim 19 wherein said analyzer is a parallel multi-channel unit adapted to generally simultaneously analyze data from two or more light beams simultaneously.

21. The mixing system according to claim 1 wherein said light source transmits an array of light beams corresponding to the array of vessels to a corresponding array of light detectors.

22. The mixing system according to claim 1 wherein each vessel of the array of vessels comprises a generally axially symmetrical bicylindrical shape having a lower compartment and an upper compartment, with the lower compartment being smaller than the upper compartment, and wherein the light beam is transmitted through a portion of the upper compartment extending beyond the periphery of the lower compartment of each of said vessels.

23. The mixing system of claim 22 wherein the magnetic stirrer elements are generally cylindrical and placed into the lower compartment of each vessel of said array.

24. The mixing system of claim 23 wherein the sample material comprises a compressed pellet placed in an opening in the magnetic stirrer element.

25. The mixing system of claim 1 wherein:
(a) each vessel of the array of vessels comprises a two chamber system including a donor compartment in which said sample material is placed, a receiver compartment, and a filter supported membrane barrier between said donor compartment and said receiver compartment;
(b) each of said donor compartment and said receiver compartment includes a magnetic stirrer element therein;
(c) each of said magnetic drive elements includes a component associated with the magnetic stirrer element in the donor compartment and a component associated with the magnetic stirrer element in the receiver compartment such that movement of the magnetic drive element by said drive mechanism causes movement of both the magnetic stirrer element in the donor compartment and the magnetic stirrer element in the receiver compartment;
(d) the compartments are configured such that the light beam can be transmitted through the receiver compartment of each of said vessels to measure the concentration of sample material transported through said membrane barrier; and
(e) said membrane barrier comprising a lipid material, a phospholipid material, or a mixture thereof, or a confluent monolayer of cultured or primary cells.

26. A method of evaluating physicochemical properties of sample materials contained as solutions or suspensions of unknown concentration in an array of vessels, comprising:
simultaneously stirring the sample material in each of said array of vessels; and
measuring a concentration-related property of a sample material contained in one of the array of vessels in situ as a function of time without invasive insertion of probes in the sample material while the sample materials are being stirred.

27. The method of claim 26 further comprising:
preparing a calibration that establishes a functional relationship between a known concentration of the sample material and said concentration-related property;
determining concentration of the sample material in the said array of vessels as a function of time by comparing said concentration-related property with said calibration; and
obtaining physicochemical properties of the sample material from the determined concentration of the sample material as a function of time.

28. The method of claim 27 wherein determining a concentration-related property of a sample material contained in a vessel comprises measuring the concentration of sample material transported through a membrane barrier from a donor compartment to a receiver compartment in said vessel.

29. The method of claim 26 wherein simultaneously stirring the sample materials in each of said array of vessels comprises moving each of a plurality of magnetic stirrer elements placed in the sample materials in each of the array of vessels by magnetically coupling said magnetic stirrer elements with corresponding magnetic drive elements, and simultaneously moving said magnetically drive elements.

30. The method of claim 29 wherein said magnetic stirrer elements comprise permanent magnets, said magnetic drive elements comprise permanent magnets, or both said magnetic stirrer elements and said magnetic drive elements comprise permanent magnets.

31. The method of claim 26 wherein measuring a concentration-related property of the sample material comprises transmitting a light beam from a light source through the sample material in each vessel to the light detector and processing data from the light detector to determine a concentration-related property of the sample material.

32. The method of claim 31 wherein the concentration-related property of the sample material in each vessel of said array of vessels is measured successively using a single light source and a single light detector.

33. The method of claim 31 wherein the concentration-related property of the sample material in each vessel of said array of vessels is measured simultaneously using multiple light sources and multiple light detectors.

34. An apparatus for evaluating physicochemical properties of sample materials contained in an array of vessels, comprising:
a light detector;
a light source for transmitting a light beam through the sample material in a vessel to the light detector;
an analyzer for processing data from the light detector to determine concentration-related properties of the sample material as a function of time; and
a mixing system, comprising:
a plurality of magnetic stirrer elements, each for being placed in a sample material in a different one of the array of vessels;
an array of magnetic drive elements, each associated with a different one of the array of vessels and being magnetically coupled with a magnetic stirrer element in an associated vessel; and
a drive mechanism coupled to the array of magnetic drive elements for simultaneously moving each of the magnetic drive elements relative to an associated vessel to cause corresponding movement of the magnetic stirrer element in the associated vessel to stir the sample material;
wherein the array of magnetic drive elements and the drive mechanism are configured to enable passage of the light beam from the light source through the sample material in each vessel to the light detector such that a concentration-related property of the sample material contained in a vessel can be detected as a function of time while the sample material is being stirred by a magnetic stirrer element.

* * * * *